US010765415B2

(12) United States Patent
Phillips

(10) Patent No.: US 10,765,415 B2
(45) Date of Patent: Sep. 8, 2020

(54) HEMOSTATIC DEVICE AND ITS METHODS OF USE

(71) Applicant: Phillips Medical, LLC, Jefferson City, MO (US)

(72) Inventor: Victor Matthew Phillips, Jefferson City, MO (US)

(73) Assignee: Phillips Medical, LLC, Jefferson City, MO (US)

( * ) Notice: Subject to any disclaimer, the term of this patent is extended or adjusted under 35 U.S.C. 154(b) by 272 days.

(21) Appl. No.: 15/975,978

(22) Filed: May 10, 2018

(65) Prior Publication Data

US 2018/0256140 A1    Sep. 13, 2018

Related U.S. Application Data

(63) Continuation of application No. 14/798,834, filed on Jul. 14, 2015, now Pat. No. 9,993,236, which is a
(Continued)

(51) Int. Cl.
*A61B 17/00* (2006.01)
*A61M 25/06* (2006.01)
*A61B 90/00* (2016.01)

(52) U.S. Cl.
CPC .. *A61B 17/0057* (2013.01); *A61B 2017/0065* (2013.01); *A61B 2017/00623* (2013.01);
(Continued)

(58) Field of Classification Search
CPC ...... A61B 17/0057; A61B 2017/00654; A61B 2017/00637; A61B 2017/00672; A61M 25/0693
See application file for complete search history.

(56) References Cited

U.S. PATENT DOCUMENTS

| 4,738,658 A | 4/1988 | Magro et al. |
| 4,850,960 A | 7/1989 | Grayzel |

(Continued)

FOREIGN PATENT DOCUMENTS

| EP | 2455110 A1 | 5/2012 |
| WO | 2011133395 A1 | 10/2011 |
| WO | 2014130107 A1 | 8/2014 |

OTHER PUBLICATIONS

Patent Examination Report No. 1, dated May 20, 2015, from the Australian patent office, for co-pending Australian patent application No. 2011243001 (4 pgs.).
(Continued)

*Primary Examiner* — Katherine M Shi
(74) *Attorney, Agent, or Firm* — Armstrong Teasdale LLP

(57) ABSTRACT

A hemostatic device for sealing a puncture of a vessel includes a first tube defining a first lumen. The first lumen is configured to receive a guidewire and a flow of a fluid therethrough. The hemostatic device also includes a second tube circumscribing at least a portion of the first tube and at least partially defining a second lumen. The hemostatic device further includes a substantially rigid stopper coupled to a distal end of the second tube. The stopper defines a stopper lumen that receives the first tube therethrough in an interference fit. A first opening is defined in a side wall of the first tube and positioned distally relative to the stopper. At least one injection groove defined in an outer surface of the stopper cooperates with the distal end of the second tube to define at least one second opening in flow communication with the second lumen.

15 Claims, 19 Drawing Sheets

Related U.S. Application Data continuation of application No. 12/762,886, filed on Apr. 19, 2010, now Pat. No. 9,179,900.

(60) Provisional application No. 61/267,685, filed on Dec. 8, 2009.

(52) U.S. Cl.
CPC .............. *A61B 2017/00654* (2013.01); *A61B 2017/00672* (2013.01); *A61B 2017/00986* (2013.01); *A61B 2090/061* (2016.02); *A61B 2090/0807* (2016.02); *A61M 25/0662* (2013.01); *A61M 25/0693* (2013.01)

(56) References Cited

U.S. PATENT DOCUMENTS

| | | | |
|---|---|---|---|
| 4,890,612 A | 1/1990 | Kensey | |
| 4,895,564 A | 1/1990 | Farrell | |
| 4,929,246 A | 5/1990 | Sinofsky | |
| 5,061,274 A | 10/1991 | Kensey | |
| 5,108,421 A | 4/1992 | Fowler | |
| 5,201,756 A | 4/1993 | Horzewski et al. | |
| 5,222,974 A | 6/1993 | Kensey et al. | |
| 5,282,827 A | 2/1994 | Kensey et al. | |
| 5,290,310 A | 3/1994 | Makower et al. | |
| 5,306,254 A | 4/1994 | Nash et al. | |
| 5,326,350 A | 7/1994 | Li | |
| RE34,866 E | 2/1995 | Kensey et al. | |
| 5,391,183 A | 2/1995 | Janzen et al. | |
| 5,415,657 A | 5/1995 | Taymor-Luria | |
| 5,431,639 A | 7/1995 | Shaw | |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,486,195 A | 1/1996 | Myers et al. | |
| 5,591,204 A | 1/1997 | Janzen et al. | |
| 5,645,566 A | 7/1997 | Brenneman et al. | |
| 5,653,730 A | 8/1997 | Hammerslag | |
| 5,665,107 A | 9/1997 | Hammerslag | |
| 5,676,689 A | 10/1997 | Kensey et al. | |
| 5,707,393 A | 1/1998 | Kensey et al. | |
| 5,716,375 A | 2/1998 | Fowler | |
| 5,725,498 A | 3/1998 | Janzen et al. | |
| 5,741,223 A | 4/1998 | Janzen et al. | |
| 5,766,157 A | 6/1998 | Tilton, Jr. | |
| 5,766,206 A | 6/1998 | Wijkamp et al. | |
| 5,782,861 A | 7/1998 | Cragg et al. | |
| 5,843,124 A | 12/1998 | Hammerslag | |
| 5,868,762 A | 1/1999 | Cragg et al. | |
| 5,935,147 A | 8/1999 | Kensey et al. | |
| 5,951,583 A | 9/1999 | Jensen et al. | |
| 5,984,950 A | 11/1999 | Cragg et al. | |
| 6,033,427 A | 3/2000 | Lee | |
| 6,045,570 A | 4/2000 | Epstein et al. | |
| 6,056,768 A | 5/2000 | Cates et al. | |
| 6,090,130 A | 7/2000 | Nash et al. | |
| 6,296,657 B1 | 10/2001 | Brucker | |
| 6,302,898 B1 | 10/2001 | Edwards et al. | |
| 6,315,753 B1 | 11/2001 | Cragg et al. | |
| 6,325,789 B1 | 12/2001 | Janzen et al. | |
| 6,350,274 B1 * | 2/2002 | Li | A61B 17/0057 604/286 |
| 6,371,974 B1 | 4/2002 | Brenneman et al. | |
| 6,371,975 B2 | 4/2002 | Cruise et al. | |
| 6,500,152 B1 | 12/2002 | Illi | |
| 6,527,734 B2 | 3/2003 | Cragg et al. | |
| 6,544,236 B1 | 4/2003 | Cragg et al. | |
| 6,547,806 B1 | 4/2003 | Ding | |
| 6,610,026 B2 | 8/2003 | Cragg et al. | |
| 6,743,248 B2 | 6/2004 | Edwards et al. | |
| 6,830,756 B2 | 12/2004 | Hnojewyj | |
| 6,863,680 B2 | 3/2005 | Ashby | |
| 6,984,219 B2 | 1/2006 | Ashby et al. | |
| 7,029,489 B1 | 3/2006 | Ashby et al. | |
| 7,037,322 B1 | 5/2006 | Sing et al. | |
| 7,048,710 B1 | 5/2006 | Cragg et al. | |
| 7,144,411 B2 | 12/2006 | Ginn et al. | |
| 7,201,725 B1 | 4/2007 | Cragg et al. | |
| 7,318,933 B2 | 1/2008 | Hnojewyj | |
| 7,335,219 B1 | 2/2008 | Ashby et al. | |
| 7,455,680 B1 | 11/2008 | Ashby et al. | |
| 7,611,479 B2 | 11/2009 | Cragg et al. | |
| 7,625,352 B1 | 12/2009 | Ashby et al. | |
| 2001/0018598 A1 | 8/2001 | Cruise et al. | |
| 2002/0062104 A1 | 5/2002 | Ashby et al. | |
| 2002/0077658 A1 | 6/2002 | Ginn | |
| 2003/0088271 A1 | 5/2003 | Cragg et al. | |
| 2003/0100921 A1 | 5/2003 | Addis et al. | |
| 2004/0019328 A1 | 1/2004 | Sing et al. | |
| 2004/0098024 A1 | 5/2004 | Dieck et al. | |
| 2004/0102730 A1 | 5/2004 | Davis et al. | |
| 2004/0176801 A1 | 9/2004 | Edwards et al. | |
| 2004/0267308 A1 | 12/2004 | Bagaoisan et al. | |
| 2005/0085854 A1 | 4/2005 | Ginn | |
| 2006/0100664 A1 | 5/2006 | Pai et al. | |
| 2006/0276838 A1 | 12/2006 | Wensel et al. | |
| 2007/0038245 A1 | 2/2007 | Morris et al. | |
| 2007/0123816 A1 | 5/2007 | Zhu et al. | |
| 2008/0038313 A1 | 2/2008 | Addis et al. | |
| 2008/0046005 A1 | 2/2008 | Lenker et al. | |
| 2008/0065152 A1 | 3/2008 | Carley | |
| 2008/0071310 A1 | 3/2008 | Hoffman et al. | |
| 2008/0082122 A1 | 4/2008 | Khosravi et al. | |
| 2008/0161849 A1 | 7/2008 | Cates et al. | |
| 2009/0088793 A1 | 4/2009 | Bagaoisan et al. | |
| 2009/0143808 A1 | 6/2009 | Houser | |
| 2009/0171282 A1 * | 7/2009 | Pipenhagen | A61B 17/0057 604/103.01 |
| 2009/0264922 A1 * | 10/2009 | Mas | A61B 17/0057 606/216 |
| 2010/0228185 A1 * | 9/2010 | Roorda | A61B 17/0057 604/48 |
| 2010/0312273 A1 | 12/2010 | Kim | |
| 2011/0137338 A1 | 6/2011 | Phillips | |
| 2013/0338705 A1 | 12/2013 | Phillips | |
| 2014/0142618 A1 | 5/2014 | Leopold et al. | |

OTHER PUBLICATIONS

Extended European Search Report of Application No. 11772458.3; dated Sep. 15, 2014; 7 pages.
Merriam-Webster dictionary definition of 'valve', Final Office Action dated Oct. 15, 2014 for U.S. Appl. No. 12/762,886, filed Apr. 19, 2010.
International Search Report and Written Opinion of PCT/US2011/032490; dated Jun. 29, 2011; 10 pages.
International Search Report and Written Opinion of International Application No. PCT/US2013/043681; dated Sep. 5, 2013; 13 pages.
Australian Second Examiner's Report, dated Sep. 29, 2015, for co-pending AU patent application No. AU 2011243001 (3 pgs.).
Patent Examination Report No. 3, dated Jan. 4, 2016, for co-pending AU patent application No. AU 2011243001 (3 pgs.).
International Search Report and Written Opinion, dated May 23, 2016, for co-pending International Application No. PCT/US2015/040761 (20 pgs.).

* cited by examiner

HEMOSTATIC DEVICE AND ITS METHODS OF USE

CROSS REFERENCE TO RELATED APPLICATIONS

This application claims the benefit of U.S. application Ser. No. 14/798,834, filed Jul. 14, 2015, which claims the benefit of U.S. application Ser. No. 12/762,886, filed Apr. 19, 2010, which claims priority to U.S. Provisional Application No. 61/267,685, filed Dec. 8, 2009, the disclosures of each of which are incorporated herein by reference in their entireties.

BACKGROUND OF THE INVENTION

The subject matter described herein relates generally to medical devices and, more particularly, to a hemostatic device.

Catheter introducers are known to provide an access site to an artery for at least some medical procedures such as cardiac catheterizations or peripheral endovascular procedures. After such medical procedures are conducted, the catheter introducer is removed from the access site, leaving an arterial opening. Generally, excess blood loss endangers and/or traumatizes the patient. One known method of controlling blood loss is through direct manual pressure over the access site.

BRIEF SUMMARY OF THE INVENTION

In one aspect, a method for sealing a puncture of a vessel using a hemostatic device is provided. The hemostatic device includes a first tube defining a first lumen configured to receive a guidewire and a flow of a fluid therethrough. The hemostatic device also includes a second tube circumscribing at least a portion of the first tube and at least partially defining a second lumen. The hemostatic device further includes a substantially rigid stopper coupled to a distal end of the second tube. The stopper defines a stopper lumen that receives the first tube therethrough in an interference fit. The method includes advancing a distal end of the hemostatic device along the guidewire into the vessel until a fluid is channeled through a first opening into the first lumen. The first opening is defined in a side wall of the first tube and positioned distally relative the stopper. The method also includes dispensing a flowable hemostatic agent through the second lumen and out of at least one second opening. At least one injection groove defined in an outer surface of the stopper cooperates with the distal end of the second tube to define the at least one second opening.

In another aspect, a hemostatic device for sealing a puncture of a vessel is provided. The hemostatic device includes a first tube defining a first lumen. The first lumen is configured to receive a guidewire and a flow of a fluid therethrough. The hemostatic device also includes a second tube circumscribing at least a portion of the first tube and at least partially defining a second lumen. The hemostatic device further includes a substantially rigid stopper coupled to a distal end of the second tube. The stopper defines a stopper lumen that receives the first tube therethrough in an interference fit. A first opening is defined in a side wall of the first tube and positioned distally relative to the stopper. At least one injection groove defined in an outer surface of the stopper cooperates with the distal end of the second tube to define at least one second opening in flow communication with the second lumen.

DETAILED DESCRIPTION OF THE INVENTION

The methods and apparatus described herein relate to medical devices and, more particularly, to a hemostatic device. The hemostatic device described herein facilitates sealing a puncture of a vessel. More particularly, the hemostatic device enables positioning an injection tube adjacent the vessel to inject a gelatin through the injection tube. As such, the hemostatic device facilitates reducing a time required for hemostasis and ambulation.

Figure 1:
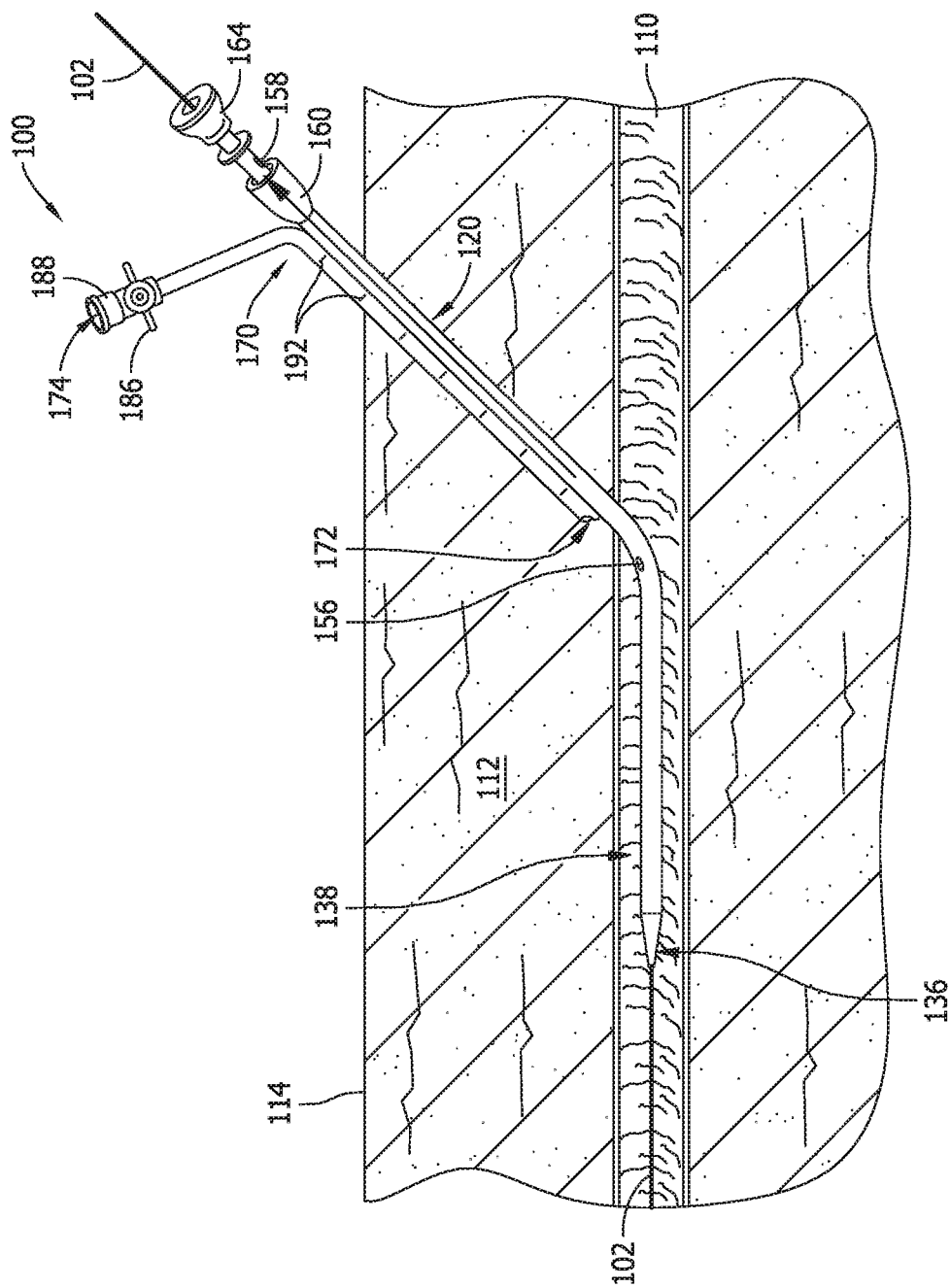
FIG. 1 is a partial cross-sectional view of an access site including an exemplary hemostatic device.
Figure 2:
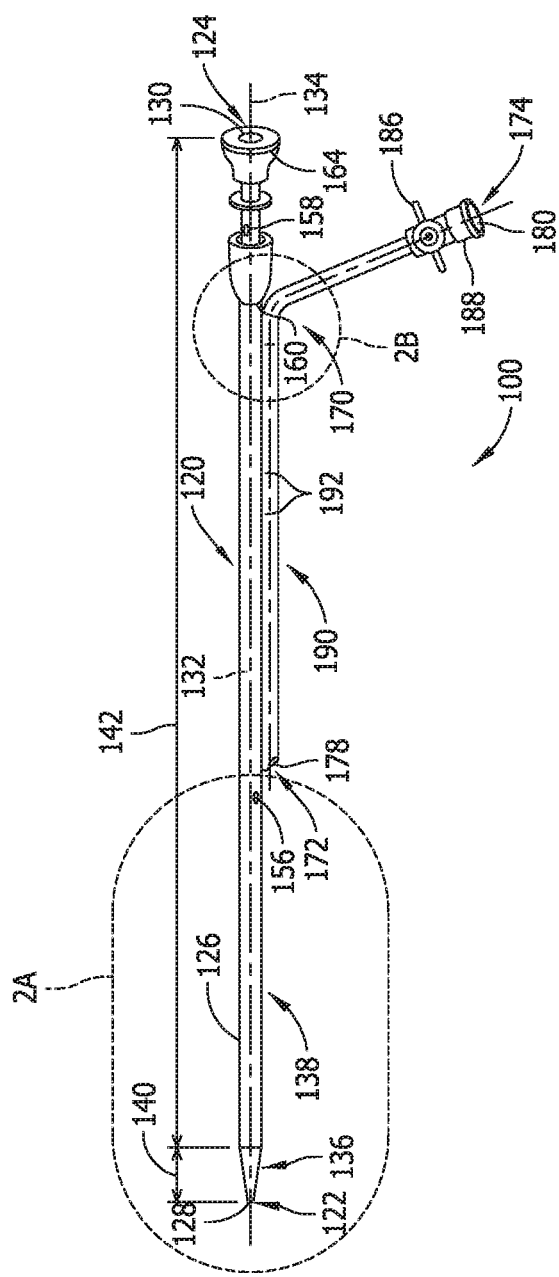
FIG. 2 is a perspective view of the hemostatic device shown in FIG. 1.
Figure 2A:
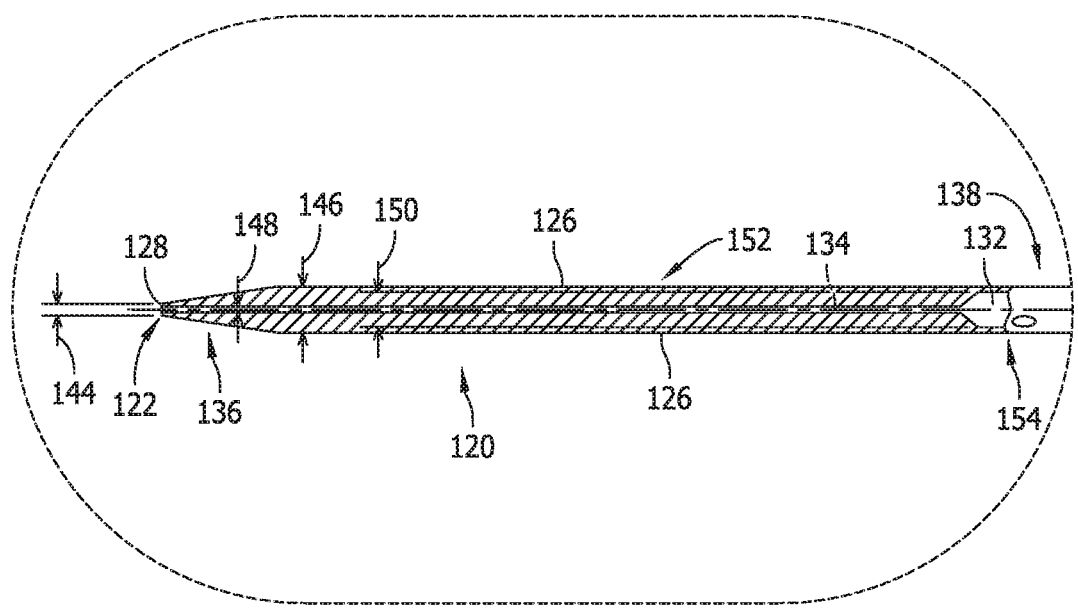
FIGS. 2A and 2B are cut-away views of the hemostatic device shown in FIG. 1.
Figure 2B:
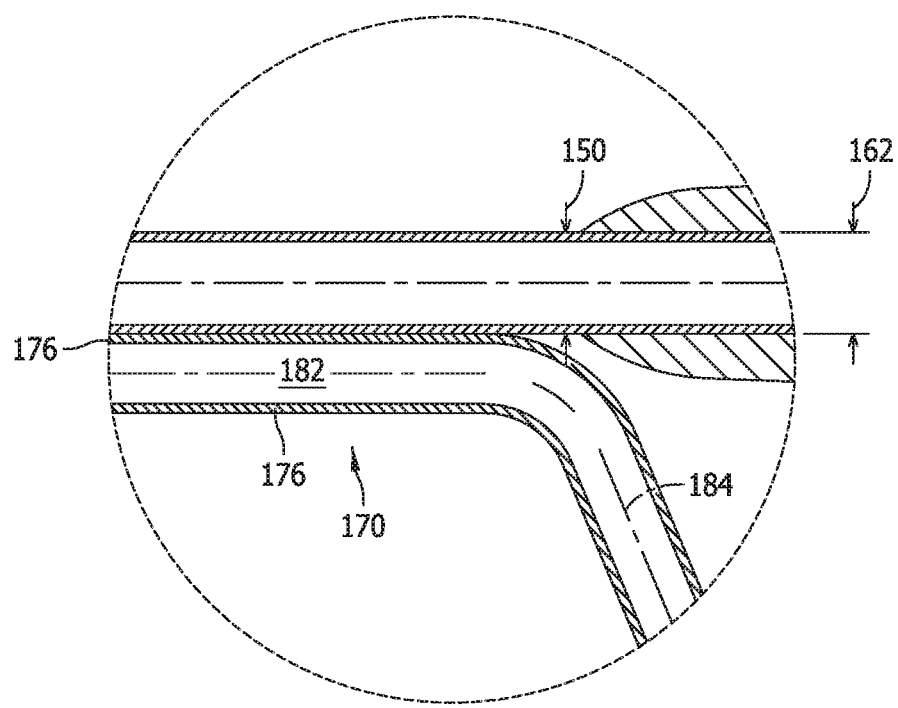

FIG. 1 is a partial cross-sectional view of an access site including an exemplary hemostatic device 100, a guidewire 102, and a vessel or, more particularly, an artery 110 within subcutaneous tissue 112 under a skin surface 114. FIG. 2 is a perspective view of hemostatic device 100, and FIGS. 2A and 2B are detailed cut-away views of hemostatic device 100. In the exemplary embodiment, hemostatic device 100 includes a locator device 120 having a distal end 122 and a proximal end 124. In the exemplary embodiment, locator device 120 extends longitudinally approximately 20.0 centimeters (cm) from distal end 122 to proximal end 124.

In the exemplary embodiment, locator device 120 includes a sidewall 126 having a distal end opening 128, a proximal end opening 130, and a lumen 132 defined therebetween substantially aligned along a center axis 134. In the exemplary embodiment, lumen 132 is configured to channel a first fluid therethrough.

In the exemplary embodiment, locator device 120 includes a first section 136 and a second section 138. First section 136 extends longitudinally a first distance 140 from distal end 122, and second section 138 extends longitudinally a second distance 142 from proximal end 124. First distance 140 is at least approximately 0.5 cm, and second distance 142 is at most approximately 19.5 cm. More particularly, in the exemplary embodiment, first distance 140 is approximately 1.0 cm, and second distance 142 is approximately 19.0 cm.

In the exemplary embodiment, locator device 120 is tapered at distal end 122 to facilitate traversing locator device 120 under skin surface 114 and through subcutaneous tissue 112. First section 136 has a first outer diameter 144, and second section 138 has a second outer diameter 146 that is larger than first outer diameter 144. Second outer diameter 146 is approximately 2 millimeters (mm) or 6 French (Fr). In another embodiment, second outer diameter 146 is approximately 2.67 mm or 8 Fr. In yet another embodiment, second outer diameter 146 is approximately 3.33 mm or 10 Fr.

In the exemplary embodiment, locator device 120 is configured to receive guidewire 102 that extends longitudinally therethrough. More specifically, distal end opening 128, first section 136, second section 138, and proximal end opening 130 are sized such that guidewire 102 is capable of extending longitudinally through lumen 132 between proximal end opening 130 and distal end opening 128. In the exemplary embodiment, guidewire 102 has an outer diameter of approximately 0.035 inches or 0.089 cm.

In the exemplary embodiment, first section 136 has a first inner diameter 148 that is approximately 0.089 cm, and second section 138 has a second inner diameter 150 that is larger than approximately 0.089 cm. More specifically, in the exemplary embodiment, second section 138 has a first subsection 152 that has first inner diameter 148 and a second subsection 154 that has second inner diameter 150. In one embodiment, second inner diameter 150 is approximately 0.059 inches or 0.150 cm. In another embodiment, second inner diameter 150 is approximately 0.087 inches or 0.221 cm. In yet another embodiment, second inner diameter 150 is approximately 0.113 inches or 0.287 cm.

As shown in FIG. 1, sidewall 126 includes a distal opening 156 and a proximal opening 158 extending radially therethrough. Distal opening 156 and proximal opening 158 are in fluid communication with lumen 132. In the exemplary embodiment, distal opening 156 and proximal opening 158 are positioned within second section 138. More specifically, in the exemplary embodiment, first subsection 152 extends longitudinally between first section 136 and distal opening 156, and second subsection extends longitudinally between distal opening 156 and proximal end 124. In the exemplary embodiment, distal opening 156 is positioned approximately 8.0 cm from distal end 122, and proximal opening 158 is positioned approximately 1.0 cm from proximal end 124.

In the exemplary embodiment, locator device 120 includes a first device valve 160 positioned adjacent proximal opening 158. First device valve 160 is actuatable between an open position and a closed position to selectively restrict access to a portion of locator device 120. In the open position, proximal opening 158 is at least partially exposed such that the fluid may flow into and/or out from lumen 132 through proximal opening 158. In contrast, in the closed position, proximal opening 158 is substantially covered by first device valve 160 such that a fluid is restricted from flowing into and/or out from lumen 132 through proximal opening 158. In the exemplary embodiment, first device valve 160 is a sleeve that has an inner diameter 162 that is larger than second outer diameter 146 such that first device valve 160 is slidable about second section 138. In the exemplary embodiment, first device valve 160 extends longitudinally approximately 1.0 cm about locator device 120.

Additionally, in the exemplary embodiment, locator device 120 includes a second device valve 164 positioned adjacent proximal end opening 130. Second device valve 164 is actuatable between an open position and a closed position to selectively restrict access to a portion of locator device 120. In the open position, proximal end opening 130 is at least partially exposed such that guidewire 102 may extend through proximal end opening 130. In contrast, in the closed position, proximal end opening 130 is substantially covered by second device valve 164 such that a fluid is restricted from flowing into and/or out from lumen 132 through proximal end opening 130. In the exemplary embodiment, second device valve 164 is a manual-adjusting valve.

In the exemplary embodiment, hemostatic device 100 further includes an injection tube 170 having a distal end 172 and a proximal end 174. Injection tube 170 extends longitudinally at least approximately 6.0 cm from distal end 172 to proximal end 174. More particularly, injection tube 170 extends longitudinally approximately 8.0 cm from distal end 172 to proximal end 174. Injection tube 170 includes a sidewall 176 having a distal end opening 178, a proximal end opening 180, and a lumen 182 defined therebetween. In the exemplary embodiment, distal end opening 178, proximal end opening 180, and lumen 182 are substantially aligned along a center axis 184, and lumen 182 is configured to channel a second fluid therethrough.

In the exemplary embodiment, injection tube 170 is coupled to locator device 120 such that distal end 172 of injection tube 170 is positionable substantially adjacent artery 110. More specifically, when distal opening 156 of locator device 120 is positioned within artery 110, distal end 172 is positionable substantially adjacent, and outside, artery 110. Distal end 172 of injection tube 170 is positioned approximately 9.0 cm from distal end 122 of locator device 120 such that distal end 172 is positioned approximately 1.0 cm from distal opening 156. In one embodiment, locator device 120 and injection tube 170 are substantially concentric.

In the exemplary embodiment, injection tube 170 includes a tube valve 186 positioned adjacent proximal end opening 180. Tube valve 186 is actuatable between an open position and a closed position to selectively restrict access to a portion of tube valve 186. In the open position, proximal end opening 180 is at least partially exposed such that the fluid may flow into and/or out from lumen 182 through proximal end opening. In contrast, in the closed position, proximal end opening 180 is substantially covered by tube valve 186 such that a fluid is restricted from flowing into and/or out from lumen 182 through proximal end opening 180. In the exemplary embodiment, tube valve 186 is a stop cock and includes a side port 188. In the exemplary embodiment, the fluid may be injected into lumen 182 through side port 188.

Injection tube 170 includes an indicator 190 that indicates a length of locator device 120 and/or injection tube 170. More specifically, indicator 190 provides an indication of how much of injection tube 170 is under skin surface 114. In the exemplary embodiment, indicator 190 includes a plurality of markings 192 that are spaced evenly along injection tube 170. More specifically, in the exemplary embodiment, there is at least one marking 192 for each centimeter of injection tube 170.

Figure 3:
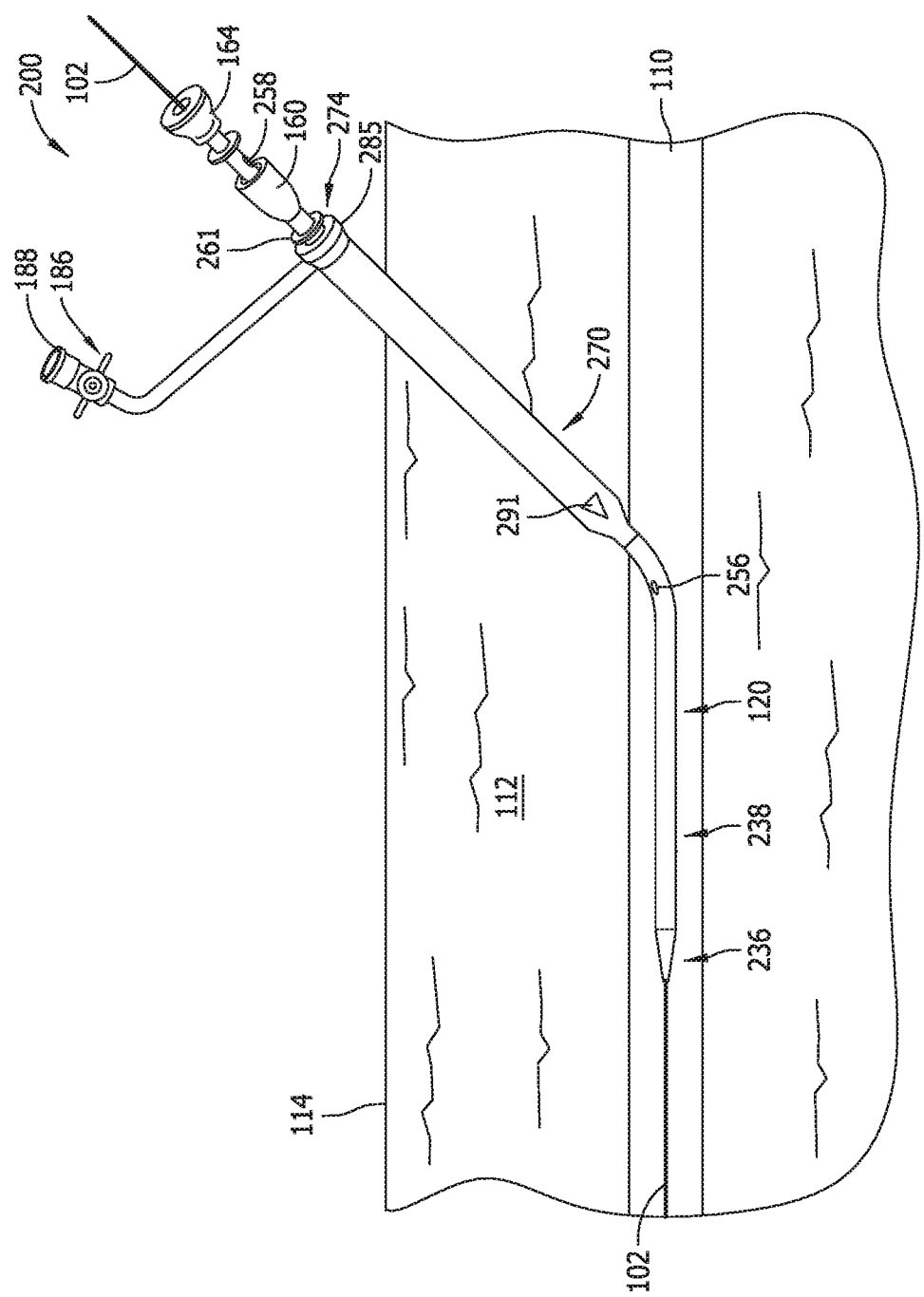
FIG. 3 is a partial cross-sectional view of an access site including an alternative hemostatic device.
Figure 4:
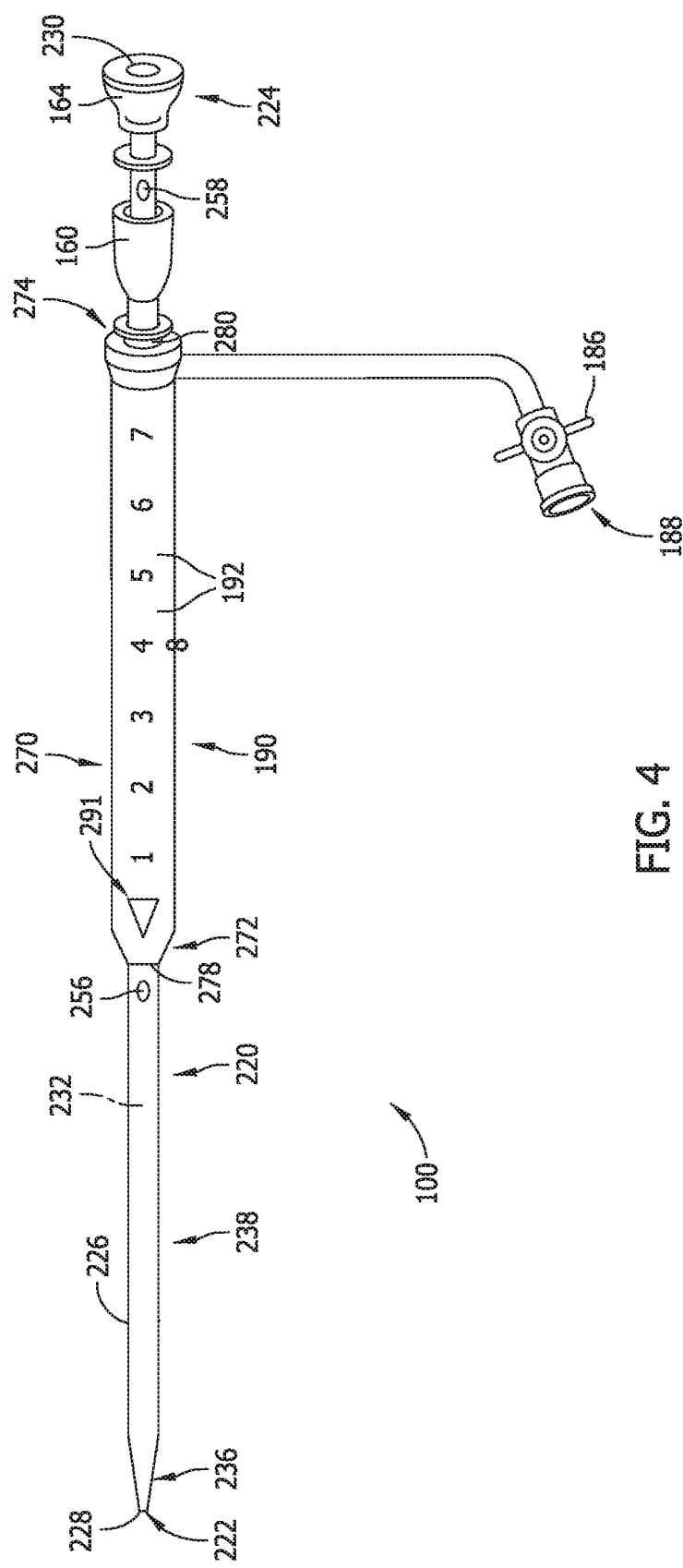
FIG. 4 is a perspective view of the hemostatic device shown in FIG. 3.
Figure 5:
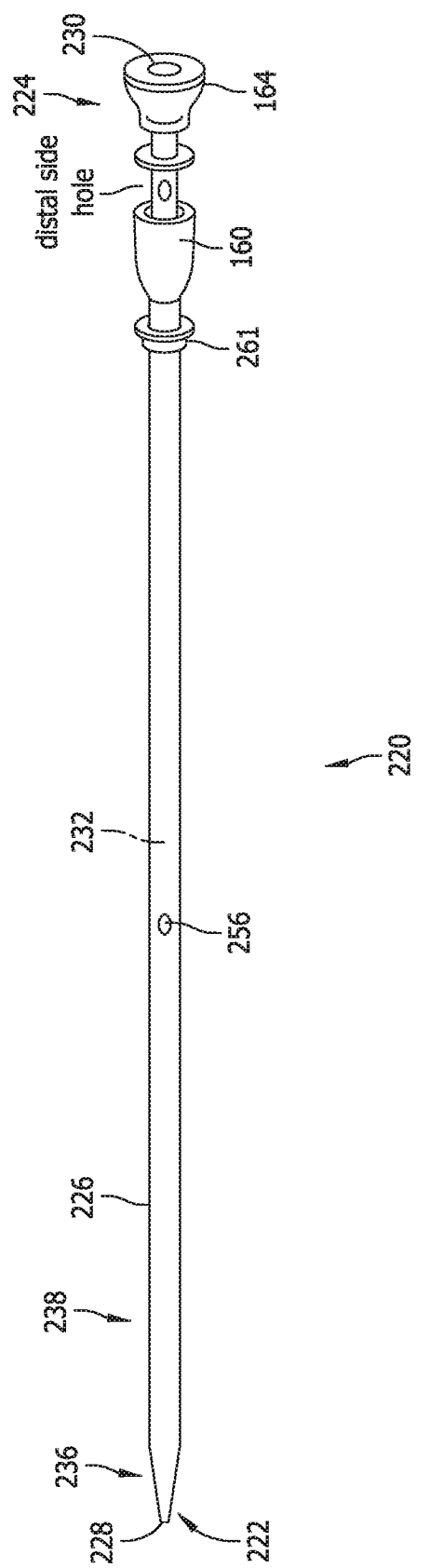
FIG. 5 is a perspective view of a locator device that may be used with the hemostatic device shown in FIG. 3.

FIG. 3 is a partial cross-sectional view of the access site including an alternative hemostatic device 200. FIG. 4 is a perspective view of hemostatic device 200. In the exemplary embodiment, hemostatic device 200 includes a locator device 220, also shown in FIG. 5, that is substantially similar to locator device 120 described in more detail above. In the exemplary embodiment, locator device 220 includes a distal end 222 and a proximal end 224. Distal end 222 is tapered to facilitate traversing locator device 220 under skin surface 114 and through subcutaneous tissue 112.

Figure 6:
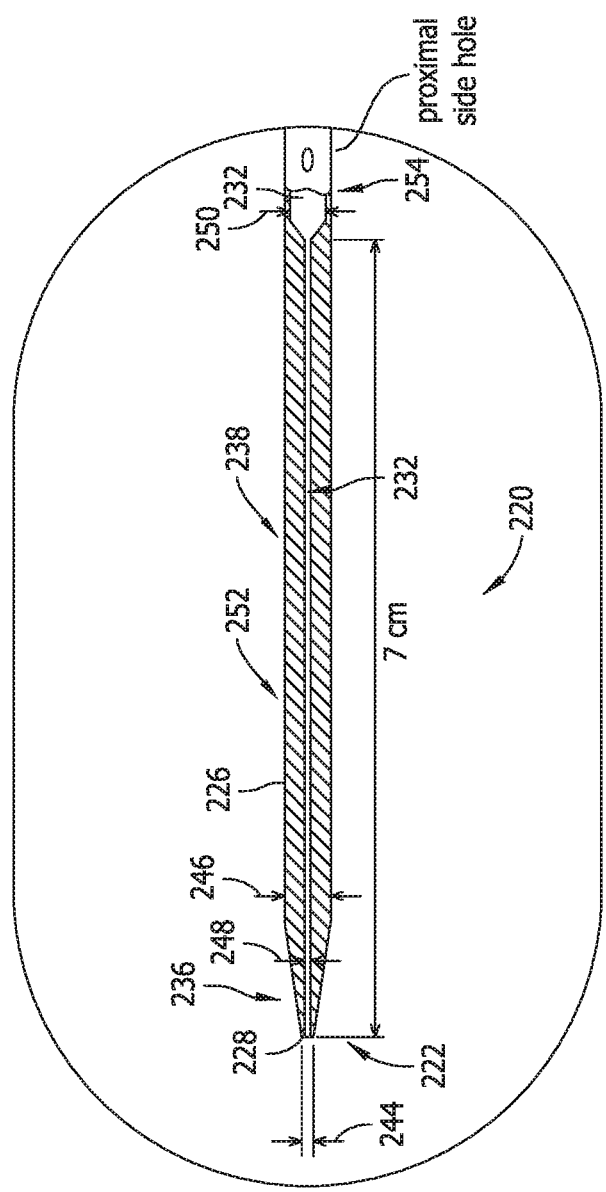
FIG. 6 is a cut-away view of the locator device shown in FIG. 5.

In the exemplary embodiment, locator device 220 includes a sidewall 226 having a distal end opening 228, a proximal end opening 230, and a lumen 232 defined therebetween sized to channel the first fluid therethrough. More specifically, as shown in FIG. 6, locator device 220 includes first section 236 having a first outer diameter 244, and a second section 238 having a second outer diameter 246 that is larger than first outer diameter 244. In one embodiment, second outer diameter 246 is approximately 0.099 inches or 0.251 cm for the 6 Fr system. In another embodiment, second outer diameter 246 is approximately 0.125 inches or 0.318 cm for the 8 Fr system. Alternatively, second outer diameter 246 may be any suitable width that enables locator device 220 to function as described herein.

Moreover, as shown in FIG. 6, first section 236 has a first inner diameter 248 that is approximately 0.889 mm, and second section 238 has a second inner diameter 250 that is sized to enable an inner flow lumen to be defined around guidewire 102. More specifically, in the exemplary embodiment, second section 238 has a first subsection 252 that has first inner diameter 248 and a second subsection 254 that has second inner diameter 250 that is larger than first inner diameter 248. In the exemplary embodiment, first subsection 252 extends longitudinally approximately 7.0 cm from distal end 222. In one embodiment, second inner diameter 250 is approximately 0.081 inches or 0.206 cm for the 6 Fr system. In another embodiment, second inner diameter 250 is approximately 0.107 inches or 0.272 cm for the 8 Fr system. Alternatively, second inner diameter 250 may be any suitable width that enables locator device 220 to function as described herein.

In the exemplary embodiment, sidewall 226 includes a distal opening 256 and a proximal opening 258 extending radially therethrough. Distal opening 256 and proximal opening 258 are in fluid communication with lumen 232. In the exemplary embodiment, distal opening 256 and proximal opening 258 are positioned within second section 238. More specifically, in the exemplary embodiment, first subsection 252 extends longitudinally between first section 236 and distal opening 256, and second subsection extends longitudinally between distal opening 256 and proximal end 224. In the exemplary embodiment, distal opening 256 is positioned approximately 8.0 cm from distal end 222, and proximal opening 258 is positioned approximately 3.0 cm from proximal end 224. Alternatively, distal opening 256 and proximal opening 258 may be positioned at any suitable location that enables locator device 220 to function as described herein.

In the exemplary embodiment, first device valve 160 is positioned adjacent proximal opening 258. First device valve 160 is actuatable between the open position and the closed position to selectively restrict access to at least a portion of locator device 220, as described in more detail above with respect to locator device 120. Moreover, in the exemplary embodiment, second device valve 164 is positioned adjacent proximal end opening 230. Second device valve 164 is actuatable between the open position and the closed position to selectively restrict access to a portion of locator device 220, as described in more detail above with respect to locator device 120.

Figure 7:
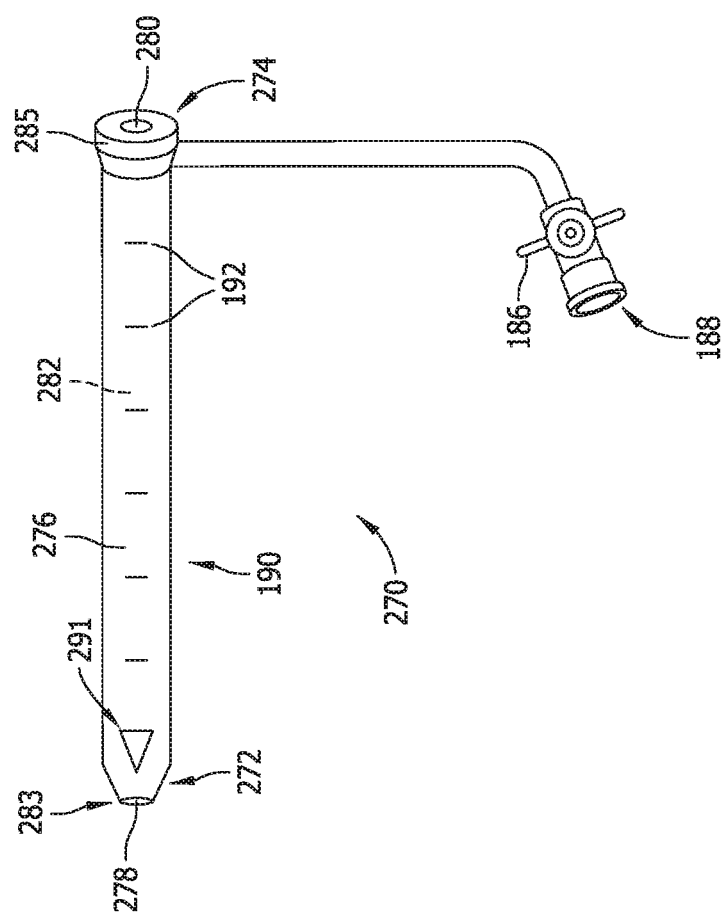
FIG. 7 is a perspective view of an injection tube that may be used with the hemostatic device shown in FIG. 3.

Locator device 220 includes a cap 261 coupleable to an injection tube 270, also shown in FIG. 7, that is substantially similar to injection tube 170. In the exemplary embodiment, injection tube 270 has a distal end 272 and a proximal end 274. Injection tube 270 is tapered at distal end 272 to facilitate traversing injection tube 270 under skin surface 114 and through subcutaneous tissue 112.

Injection tube 270 includes a sidewall 276 having a distal end opening 278, a proximal end opening 280, and a lumen 282 defined therebetween. In the exemplary embodiment, distal end opening 278 includes a distal valve 283 configured to receive locator device 220 such that locator device 220 and injection tube 270 are substantially coaxial. More specifically, in the exemplary embodiment, locator device 220 is advanceable through distal valve 283 such that injection tube 270 substantially houses at least a portion of locator device 220. In the exemplary embodiment, locator device 220 is advanced until a proximal valve 285 positioned at injection tube proximal end 274 is coupled to cap 261 such that injection tube distal end 272 may be positioned substantially adjacent distal opening 256. In the exemplary embodiment, injection tube distal end 272 is positionable approximately 9.0 cm from locator device distal end 222 and/or approximately 1.0 cm from locator device distal opening 256. As such, when locator device distal opening 256 is positioned within artery 110, injection tube distal end 272 is positioned substantially adjacent, and outside, artery 110.

In the exemplary embodiment, injection tube 270 has a first inner diameter 287 adjacent distal end 272 that is substantially similar to locator device second outer diameter 246. In one embodiment, first inner diameter 287 is approximately 0.099 inches or 0.251 cm for the 6 Fr system. In another embodiment, first inner diameter 287 is approximately 0.125 inches or 0.318 cm for the 8 Fr system. In the exemplary embodiment, injection tube 270 has a second inner diameter 289 that is sized to channel the second fluid through lumen 282 about locator device 220. As such, second inner diameter 289 is wider than first inner diameter 287 or, more specifically, locator device second outer diameter 246 in the exemplary embodiment. In one embodiment, second inner diameter 289 is approximately 0.139 inches or 0.353 cm for the 6 Fr system. In another embodiment, second inner diameter 289 is approximately 0.165 inches or 0.419 cm for the 8 Fr system.

In the exemplary embodiment, side port 188 extends from injection tube 270 and is communicatively coupled to lumen 282. Side port 188 includes tube valve 186 that is actuatable between the open position and the closed position to selectively restrict access to a portion of tube valve 186, as described in more detail above with respect to injection tube 170. The second fluid is injectable into side port 188, through lumen 282, and discharged from a plurality of side openings 291 extending through sidewall 276. Side openings 291 are spaced substantially evenly about a circumference of injection tube 270. For example, in one embodiment, side openings 289 are positioned at each quadrant of sidewall 276.

In the exemplary embodiment, side openings 291 are positioned adjacent distal opening 156. More specifically, side openings 291 are spaced between approximately 5.0 mm and 10.0 mm from a distal end of injection tube 270. As such, when distal opening 256 is positioned within artery 110, side openings 291 are positionable substantially adjacent, and outside, artery 110 to facilitate sealing the puncture of artery 110.

Figure 8:
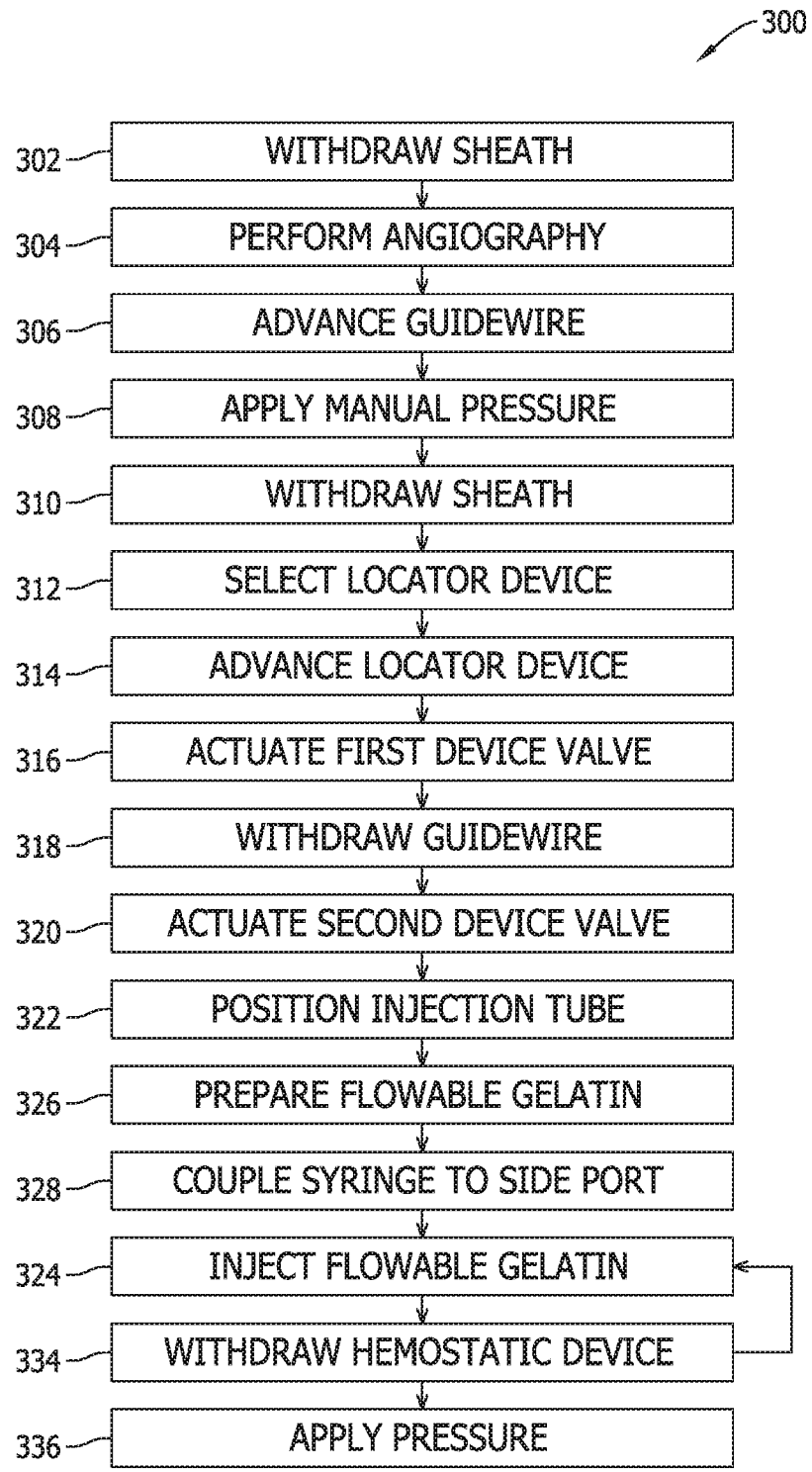
FIG. 8 is a flow chart illustrating an exemplary method of using the hemostatic device shown in FIG. 1 and/or FIG. 3.

FIG. 8 is a flow chart illustrating an exemplary method 300 using hemostatic device 100 and/or 200. During operation, hemostatic device 100 and/or 200 is used for sealing a puncture of artery 110 within subcutaneous tissue 112 under a skin surface 114.

In the exemplary embodiment, a sheath (not shown) used during a medical procedure, such as a cardiac catheterization or a peripheral endovascular procedure, is withdrawn 302 such that a tip of the sheath is positioned approximately 10.0 cm from the access site and the sheath is free of at least some devices. A limited angiography is performed 304 through the sheath to assess the puncture of artery 110 and to ensure that the sheath is positioned within artery 110.

In the exemplary embodiment, guidewire 102 is advanced 306 through the sheath to artery 110 such that a tip of guidewire 102 is positioned at least approximately 5.0 cm beyond the tip of the sheath. More particularly, guidewire 102 is advanced 306 to position the tip of guidewire 102 approximately 10.0 cm beyond the tip of the sheath. Manual pressure is applied 308 over the access site, and the sheath is withdrawn 310 from the access site over guidewire 102. Locator device 120 and/or 220 is determined or selected 312 based on a size of the sheath. For example, in one embodiment, locator device 120 and/or 220 is selected 312 to have an outer diameter that is approximately the same as an outer diameter of the sheath. More specifically, in such an embodiment, the 6 Fr system may be used with, without limitation, a sheath having a diameter between approximately 4 Fr and 6 Fr, and the 8 Fr system may be used with, without limitation, a sheath having a diameter between approximately 6 Fr and 8 Fr.

In the exemplary embodiment, locator device 120 and/or 220 is advanced 314 into artery 110 until a first fluid is channeled through locator device 120 and/or 220. More specifically, in the exemplary embodiment, locator device 120 and/or 220 is advanced 314 or slid along guidewire 102 under skin surface 114, through subcutaneous tissue 112, and to artery 110 until distal opening 156 and/or 256 is positioned within artery 110 and a fluid such as blood flows into distal opening 156 and/or 256, through lumen 132 and/or 232, and out from proximal opening 158 and/or 258. In the exemplary embodiment, locator device 120 and/or 220 is advanced 314 under skin level for approximately 8.0 cm.

Proximal opening 158 and/or 258 provides a visual cue that distal opening 156 and/or 256 is within artery 110 when the blood flows through proximal opening 158 and/or 258. To reduce an amount of blood that refluxes through proximal opening 158 and/or 258, first device valve 160 is actuated 316 to the closed position to restrict the blood from flowing out from proximal opening 158 and/or 258 and/or through lumen 132 and/or 232. Moreover, guidewire 102 is withdrawn 318 from artery 110 and/or locator device 120 and/or 220, and second device valve 164 is actuated 320 to the closed position to restrict the blood from flowing through proximal end opening 130 and/or through lumen 132 and/or 232.

Injection tube distal end 172 and/or 272 is positioned 322 substantially adjacent artery 110. More specifically, the relative positioning of locator device 120 and/or 220 and injection tube 170 and/or 270 enables injection tube distal end 172 and/or 272 to be positioned 322 substantially adjacent, and just outside, artery 110 when distal opening 156 and/or 256 is initially advanced within artery 110.

In the exemplary embodiment, a second fluid or, more particularly, a flowable gelatin is injected 324 around artery 110 and along a tract through subcutaneous tissue 112 between artery 110 and skin surface 114 through injection tube 170 and/or 270 to facilitate sealing the puncture of artery 110. More specifically, in the exemplary embodiment, the flowable gelatin is prepared 326 and received within a syringe (not shown), and the syringe is coupled 328 to injection tube side port 188.

In the exemplary embodiment, the flowable gelatin is discharged from side openings 291 to facilitate sealing the access site. The injection process may be repeated as hemostatic device 100 and/or 200 is withdrawn 334 from artery 110 a length at a time until hemostatic device 100 and/or 200 is substantially withdrawn from subcutaneous tissue 112. More specifically, in such an embodiment, hemostatic device 100 and/or 200 may be systematically positioned within subcutaneous tissue 112 based on at least one length indicated by indicator 190 to enable the flowable gelatin to be systematically injected 324 through injection tube 170 and/or 270 at each position. In one embodiment, indicator 190 provides a visual cue that a length of injection tube 170 and/or 270 is under skin surface 114 and facilitates maintaining the length and/or systematically adjusting the length. Additionally or alternatively, side port 188 may be rotated approximately 180° about center axis 134 to inject additional flowable gelatin through injection tube 170.

In the exemplary embodiment, when injection tube distal end 172 and/or 272 is substantially adjacent skin surface 114, hemostatic device 100 and/or 200 is withdrawn 334 from artery 110 and/or subcutaneous tissue 112. In the exemplary embodiment, direct, non-occlusive manual pressure is continuously applied 336 to the access site until hemostasis is achieved.

Figure 9:
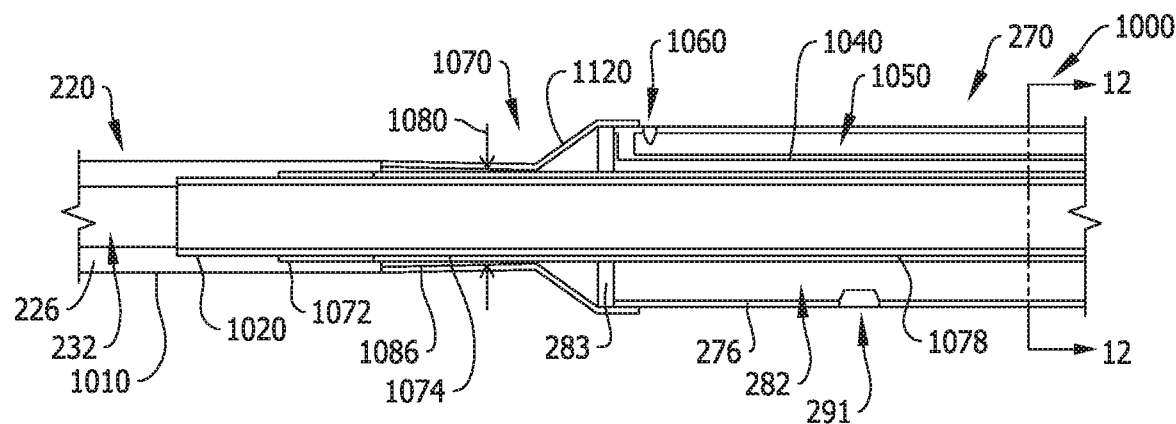
FIG. 9 is a cross-sectional view of a portion of another exemplary hemostatic device, with an exemplary malecot in a neutral configuration.
Figure 10:
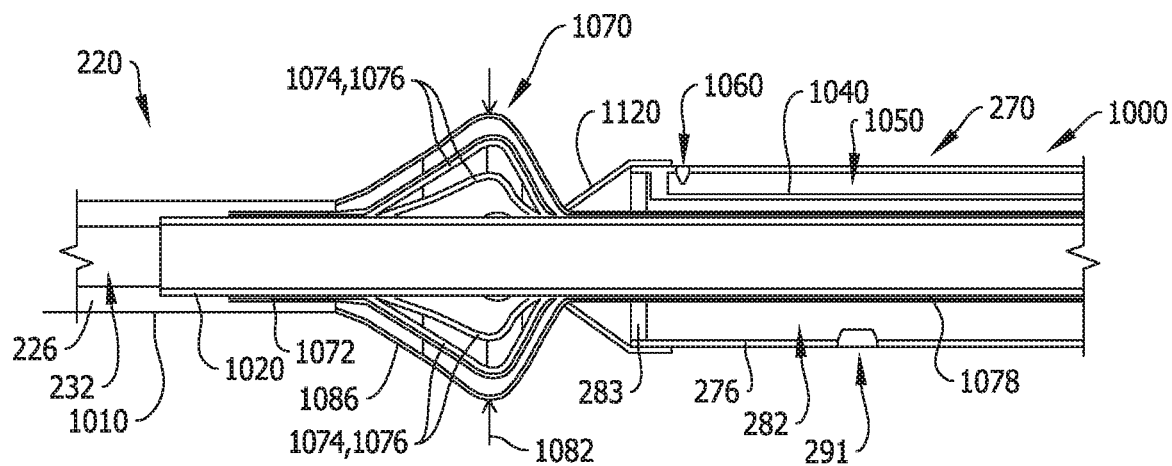
FIG. 10 is a cross-sectional view of the portion the exemplary hemostatic device shown in FIG. 9 with the exemplary malecot in a stopper configuration.

FIGS. 9 and 10 are cross-sectional views of a portion of another exemplary hemostatic device 1000 for sealing a puncture of a vessel (not shown). Hemostatic device 1000 is similar to hemostatic device 100 and 200 and, in the absence of a contrary representation, the same reference numbers identify the same or similar elements. Hemostatic device 1000 includes locator device 220, and injection tube 270. In the exemplary embodiment, second section 238 of locator device 220 includes a distal portion 1010 and a proximal portion 1020. In other embodiments, second section 238 may include any suitable number of portions. In the exemplary embodiment, distal portion 1010 and proximal portion 1020 are coupled coaxially and in fluid communication to define lumen 232.

In certain embodiments, hemostatic device 1000 includes a transitional sleeve 1120 coupled to distal end 272 of injection tube 270. Transitional sleeve 1120 tapers distally from injection tube 270 to create a smooth transition between distal end 272 of injection tube 270 and proximal portion 1020 of locator device 220. In alternative embodiments, hemostatic device 1000 includes any suitable transition between injection tube 270 and proximal portion 1020 of locator device 220.

In the exemplary embodiment, hemostatic device 1000 includes a malecot 1070 positioned distal with respect to distal end 272 of injection tube 270, such that malecot 1070 is positionable within a lumen of a vessel and substantially adjacent a vessel access site when distal end 272 of injection tube 270 is outside and/or substantially adjacent a vessel access site.

Malecot 1070 includes a distal portion 1072 coupled to locator device 220. In the exemplary embodiment, distal portion 1072 is rigidly coupled between distal portion 1010 and proximal portion 1020 of locator device 220 by an interference fit. Alternatively, distal portion 1072 is coupled to at least one of distal portion 210 and proximal portion 220 in any configuration and/or using any mechanism that enables malecot 1070 to function as described herein.

In the exemplary embodiment, malecot 1070 also includes an expandable portion 1074 proximal to distal portion 1072. Expandable portion 1074 is disposed circumferentially about locator device 220 and distal to transitional sleeve 1120. Malecot 1070, and specifically expandable portion 1074 of malecot 1070, is selectively actuatable between a neutral configuration (shown in FIG. 9) and a stopper configuration (shown in FIG. 10). In the neutral configuration, expandable portion 1074 has a first diameter 1080. In the stopper configuration, expandable portion 1074 has a second diameter 1082 that is greater than first diameter 1080. In the exemplary embodiment, malecot 1070 is configured such that first diameter 1080 is less than a diameter of an opening in a vessel wall at a vessel access site and second diameter 1082 is greater than the diameter of the opening, as will be described herein. Thus, malecot 1070 in the stopper configuration is configured to facilitate positioning side openings 291 outside the lumen of the vessel, and adjacent to the vessel wall, prior to the release of the flowable gelatin from hemostatic device 1000, and to substantially seal the vessel wall from penetration by the flowable gelatin at the access site, as will be described herein.

As described above, distal valve 283 is configured to receive locator device 220 therethrough and to seal injection tube distal end 272, such that the flowable gelatin is at least substantially prevented from exiting lumen 282 via injection tube distal end 272 as the flowable gelatin is dispersed via side openings 291.

Figure 11:
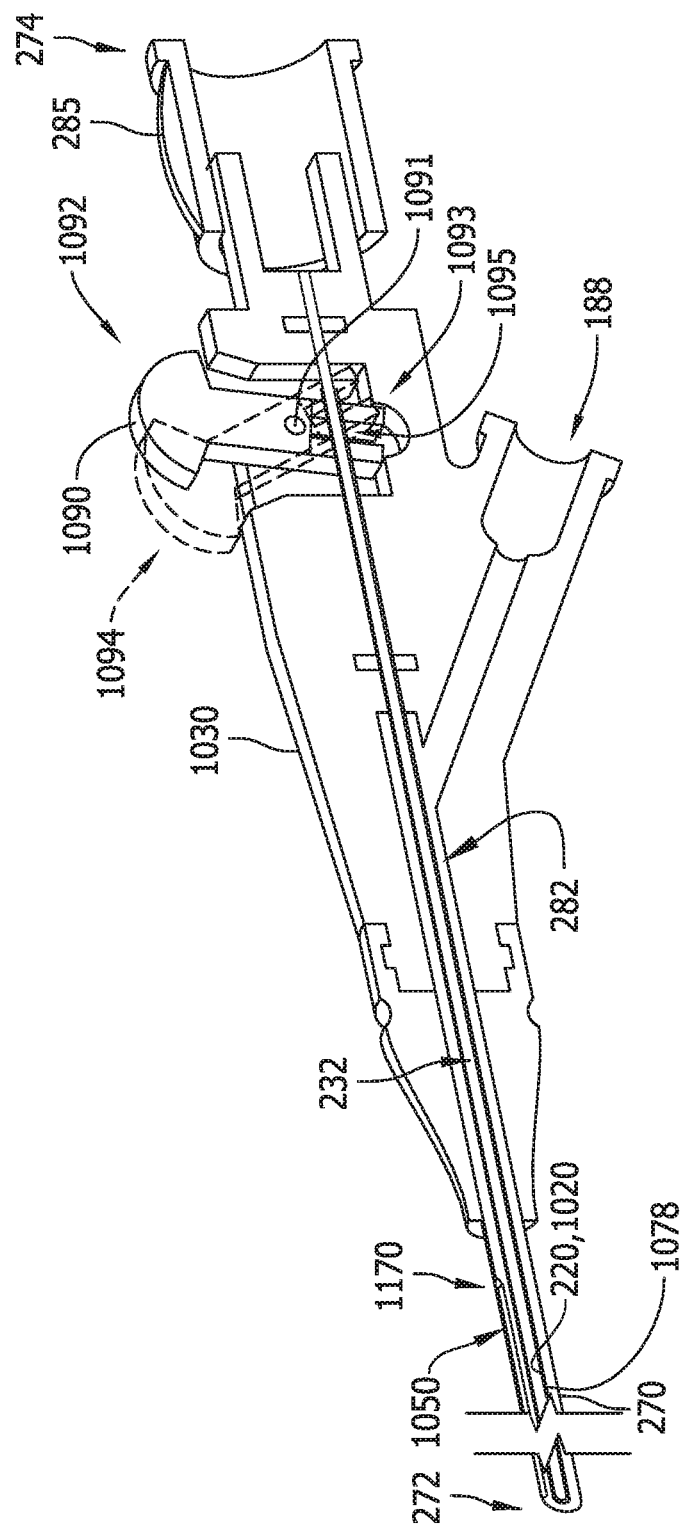
FIG. 11 is a perspective cross-sectional view of a housing of the exemplary hemostatic device shown in FIG. 9.

FIG. 11 is a perspective cross-sectional view of a housing 1030 of hemostatic device 1000, located on a proximal portion of injection tube 270. In the exemplary embodiment, housing 1030 is coaxial with locator device 220 and houses port 188 of injection tube 270, proximal end opening 280, and proximal valve 285 of locator device lumen 232. With reference to FIGS. 9-11, in certain embodiments, hemostatic device 1000 includes a plug actuator 1090 coupled to malecot 1070. In the exemplary embodiment, plug actuator 1090 also is coupled to housing 1030. In alternative embodiments, plug actuator 1090 is coupled to any suitable portion of hemostatic device 1000 that enables plug actuator 1090 to function as described herein. Plug actuator 1090 is configured to selectively actuate malecot 1070 between at least the neutral configuration (shown in FIG. 9) and the stopper configuration (shown in FIG. 10).

For example, in the exemplary embodiment, each of plug actuator 1090 and malecot 1070 is operably coupled to a transfer member 1078. Transfer member 1078 extends longitudinally between plug actuator 1090 and malecot 1070, and is selectively operable by plug actuator 1090 for longitudinal translation with respect to locator device 220. In the exemplary embodiment, transfer member 1078 is a tube disposed coaxially with, and radially outwardly from, locator device 220. In alternative embodiments, transfer member 1078 has any suitable structure that enables malecot 1070 to function as described herein.

For example, in the exemplary embodiment, plug actuator 1090 is pivotally coupled to housing 1030 at a pivot 1091, and a radially inner end 1093 of plug actuator 1090 is coupled to transfer member 1078 such that pivotal movement of plug actuator 1090 results in longitudinal translational motion of transfer member 1078. For example, but not by way of limitation, radially inner end 1093 includes a slot 1095 that cooperates with oppositely disposed, transversely extending pegs (not shown) on transfer member 1078. Alternatively, plug actuator 1090 and transfer member 1078 each include any suitable structure such that pivotal movement of plug actuator 1090 results in longitudinal translational motion of transfer member 1078.

In some embodiments, expandable portion 1074 includes a plurality of reversibly deformable segments 1076. For example, in the exemplary embodiment, deformable segments 1076 are arranged circumferentially around locator device 220, and each deformable segment 1076 extends longitudinally over a portion of locator device 220. More specifically, deformable segments 1076 extend longitudinally between malecot distal portion 1072, which is rigidly coupled to locator device 220, and a distal end of transfer member 1078. Deformable segments 1076 are configured to reversibly deform radially outward from locator device proximal portion 1020 to accommodate longitudinal translation of transfer member 1078 towards fixed malecot distal portion 1072, and to reversibly deform radially inward towards locator device proximal portion 1020 to accommodate longitudinal translation of transfer member 1078 away from fixed malecot distal portion 1072. Thus, deformable segments 1076 selectively define each of first diameter 1080 and second diameter 1082 of expandable portion 1074 in response to a respective corresponding longitudinal position of transfer member 1078 relative to locator device 220.

In the exemplary embodiment, plug actuator 1090 is selectively moveable between a first position 1092 and a second position 1094 (shown in phantom lines in FIG. 11).

In first position 1092, transfer member 1078 is longitudinally positioned with respect to locator device 220 such that deformable segments 1076 radially deform to transition malecot 1070 to the stopper configuration (shown in FIG. 10). In second position 1094, transfer member 1078 is longitudinally positioned with respect to locator device 220 such that deformable segments 1076 radially deform to transition malecot 1070 to the neutral configuration (shown in FIG. 9). In alternative embodiments, plug actuator 1090 is selectively moveable to any suitable positions to reversibly transition malecot 1070 between the neutral and stopper configurations.

In certain embodiments, transfer member 1078, malecot distal portion 1072, and expandable portion 1074 are formed unitarily from a single tube. For example, the single tube has a length equal to a combined length of transfer member 1078, expandable portion 1074 in the neutral configuration, and distal portion 1072. Deformable segments 1076 are defined on expandable portion 1074 by a plurality of circumferentially disposed, longitudinally extending slots. More specifically, each slot extends radially through a sidewall of the tube along expandable portion 1074, such that each slot separates a pair of adjacent deformable segments 1076. In alternative embodiments, each of transfer member 1078, malecot distal portion 1072, and expandable portion 1074 are fabricated from any suitable number of components coupled together in any suitable fashion that enables malecot 1070 to function as described herein.

In the exemplary embodiment, expandable portion 1074 is formed from a material that provides a desired degree of deformability to deformable segments 1076. For example, but not by way of limitation, expandable portion 1074 is fabricated from a Nitinol alloy. In some embodiments, transfer member 1078 and malecot distal portion 1072 also are formed from a Nitinol alloy. In alternative embodiments, each of transfer member 1078, malecot distal portion 1072, and expandable portion 1074 is fabricated from any suitable material that enables malecot 1070 to function as described herein.

In the exemplary embodiment, a flexible sleeve 1086 is disposed circumferentially around expandable portion 1074 to facilitate preventing interaction between deformable segments 1076 and subcutaneous tissue. For example, but not by way of limitation, sleeve 1086 is formed from an elastomer material. In alternative embodiments, hemostatic device 1000 does not include sleeve 1086.

Figure 12:
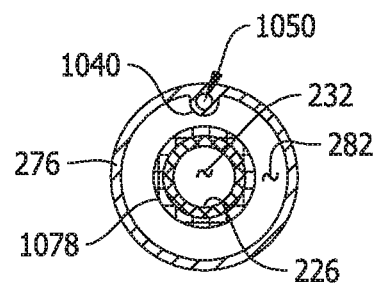
FIG. 12 is a cross-sectional view of the exemplary hemostatic device shown in FIG. 9, taken along lines 12-12 shown in FIG. 9.

FIG. 12 is a cross-sectional view of hemostatic device 1000 taken along lines 12-12 shown in FIG. 9. With reference to FIGS. 9-12, in the exemplary embodiment, hemostatic device 1000 includes a third or intermediate tube 1040 positioned radially between locator device 220 and sidewall 276 of injection tube 270. More specifically, intermediate tube 1040 is positioned such that a third or intermediate lumen 1050 configured to channel blood or, more broadly, a fluid therethrough is at least partially defined by intermediate tube 1040. In certain embodiments, intermediate lumen 1050 is in fluid communication with a first opening 1060 that extends through injection tube 270. For example, but not by way of limitation, first opening 1060 is defined in, and extends through, sidewall 276 of injection tube 270 just proximal to distal end 272. Moreover, in certain embodiments, intermediate lumen 1050 also is in fluid communication with a second opening 1170 (shown in FIG. 11), such that fluid may enter intermediate lumen 1050 through first opening 1060 and is dischargeable through second opening 1170. For example, but not by way of limitation, second opening 1170 is defined in, and extends through, sidewall 276 of injection tube 270 just distal to housing 1030. In alternative embodiments, first opening 1060 and second opening 1170 are defined in any suitable fashion, and at any suitable location, that enables intermediate lumen 1050 to function as described herein.

In certain embodiments, a reflux of blood from a lumen of a vessel through outer tube first opening 1060, intermediate lumen 1050, and second opening 1170 provides sufficient visual information regarding a position of malecot 1070 as will be described herein, such that locator device 220 need not include distal opening 256, and locator device lumen 232 is sized to accommodate a guidewire (not shown) in a clearance fit from distal end 222 to proximal end 224, rather than to additionally channel a reflux of blood. In other embodiments, hemostatic device 1000 includes distal opening 256 and lumen 232 sized to accommodate a reflux of blood, as described above, in addition to intermediate lumen 1050. In still other embodiments, hemostatic device 1000 includes distal opening 256 and lumen 232 sized to accommodate a reflux of blood, and does not include any third tube and/or third lumen.

Figure 13:
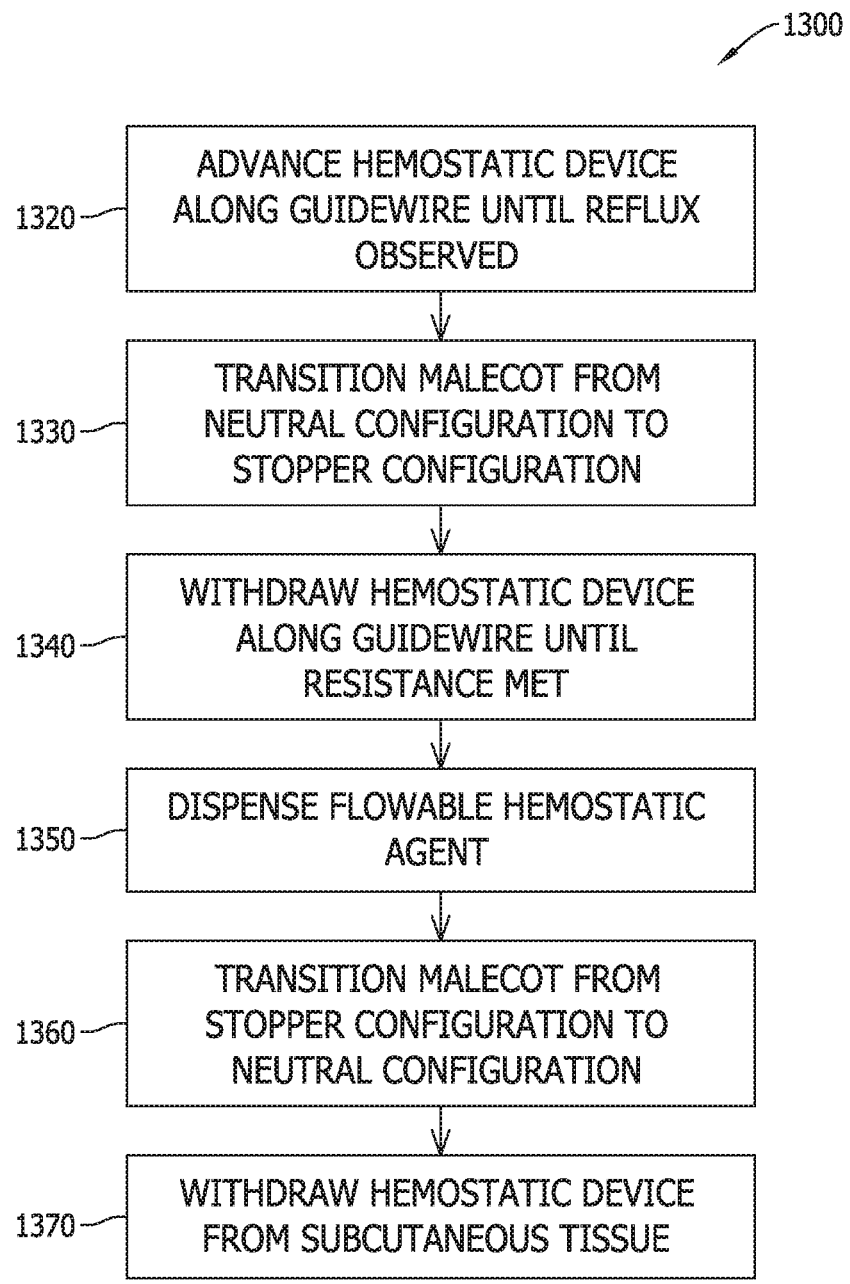
FIG. 13 is a flow chart illustrating an exemplary method of using the exemplary hemostatic device shown in FIG. 9.

FIG. 13 is a flow chart illustrating an exemplary method 1300 of using hemostatic device 1000 to seal a puncture opening 1406 in an artery or vessel 1400 with a flowable hemostatic agent 1450. FIGS. 14-19 illustrate hemostatic device 1000 during various stages of method 1300.

Figure 14:
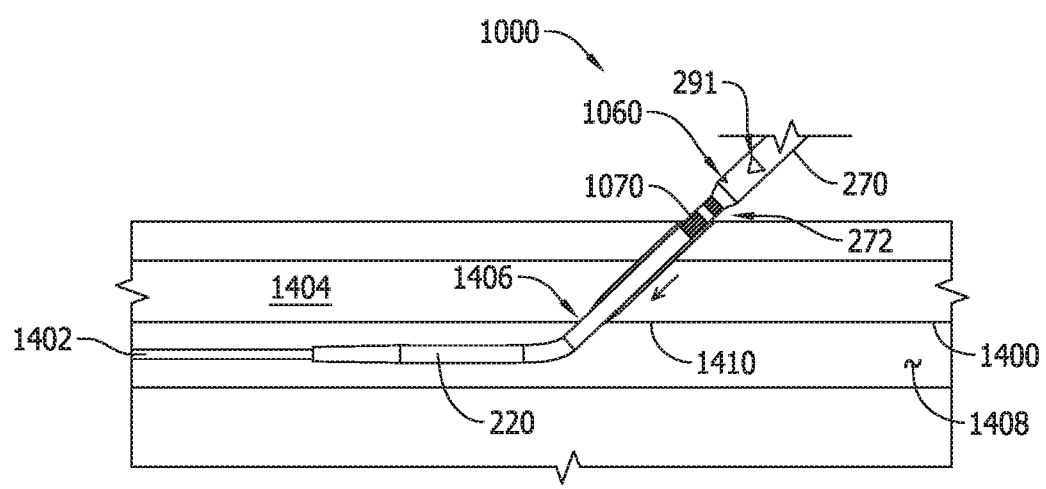
FIG. 14 is a schematic view of a portion of the hemostatic device shown in FIG. 9 being advanced into a blood vessel, with the exemplary malecot in the neutral configuration shown in FIG. 9.
Figure 15:
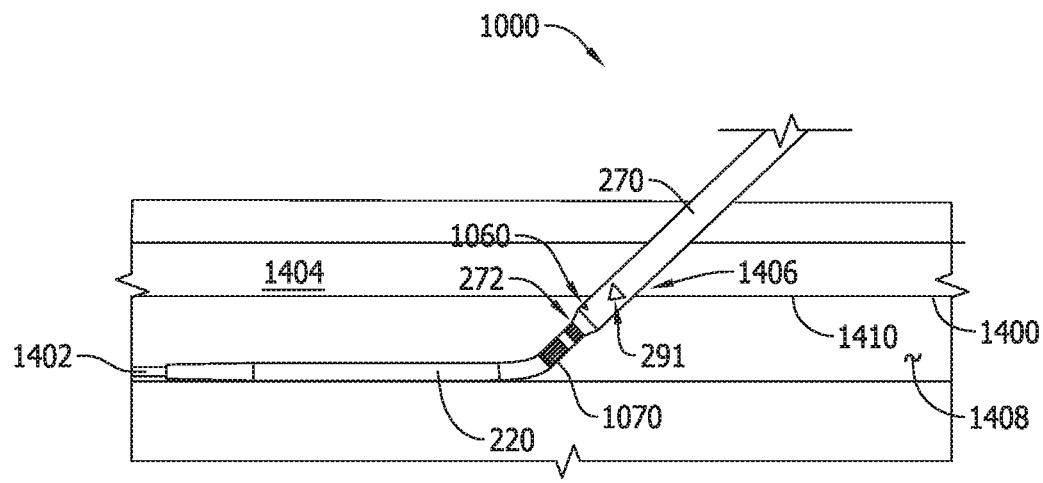
FIG. 15 is a schematic view of a portion of the hemostatic device shown in FIG. 9 with the exemplary malecot positioned within the blood vessel, and with the exemplary malecot in the neutral configuration shown in FIG. 9.

During operation, locator device 220 is aligned such that a guidewire 1402 extends through distal opening 228, lumen 232, and proximal opening 230. Malecot 1070 is positioned in the neutral position, and hemostatic device 1000 is advanced 1320 along guidewire 1402, as shown in FIG. 14, through subcutaneous tissue 1404 into lumen 1408 of vessel 1400 until blood is channeled through injection tube first opening 1060 and intermediate lumen 1050 and discharged from injection tube second opening 1170. In the exemplary embodiment, the blood discharge (i.e., reflux) from injection tube second opening 1170 is a visual indication that outer tube first opening 1060 is positioned within the vessel, as shown in FIG. 15. In at least some implementations, malecot 1070 provides a tactile indication (e.g., resistance from a wall 1410 of vessel 1400 surrounding puncture opening 1406) that injection tube distal end 272 is adjacent the vessel wall. Additionally or alternatively, in at least certain implementations, locator device 220 includes distal opening 256, and a blood discharge (i.e., reflux) from locator device proximal opening 258 is a visual indication that distal opening 256 is positioned within the vessel.

Figure 16:
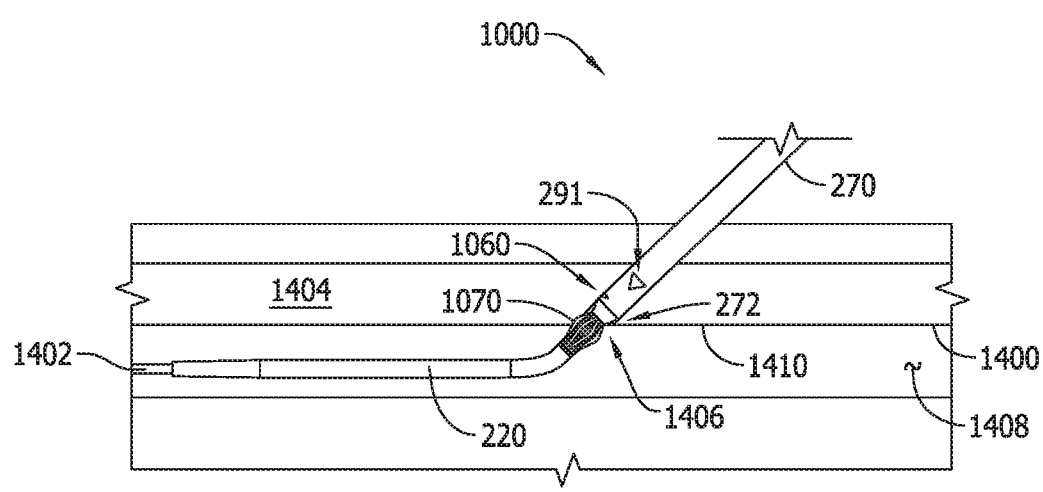
FIG. 16 is a schematic view of a portion of the hemostatic device shown in FIG. 9 with the exemplary malecot positioned within the blood vessel, and with the exemplary malecot in the stopper configuration shown in FIG. 10.

In the exemplary embodiment, plug actuator 1090 is selectively moved to first position 1092 such that malecot 1070 is transitioned 1330 from the neutral configuration to the stopper configuration. Malecot 1070 in the stopper configuration has second diameter 1082 that is greater than a diameter of opening 1406 in vessel wall 1410, which inhibits malecot 1070 from passing back through vessel wall 1410 and out of vessel lumen 1408. Hemostatic device 1000 is then withdrawn 1340 along guidewire 1402 until resistance is met, indicating that malecot 1070 is abutting an interior surface of vessel wall 1410 and, therefore, that injection tube distal end 272 has moved from inside vessel lumen 1408 to outside, and adjacent to, vessel wall 1410, as shown in FIG. 16. In at least some implementations, the position of injection tube distal end 272 outside vessel lumen 1408 is confirmed by an absence or substantial reduction of blood discharge from injection tube second opening 1170. Malecot 1070 abutting the interior surface of vessel wall 1410 facilitates ensuring that flowable hemostatic agent 1450 will be released outside vessel lumen 1408 and facilitates occluding puncture opening 1406, such that flowable hemostatic agent 1450, once released, does not enter vessel lumen 1408.

Figure 17:
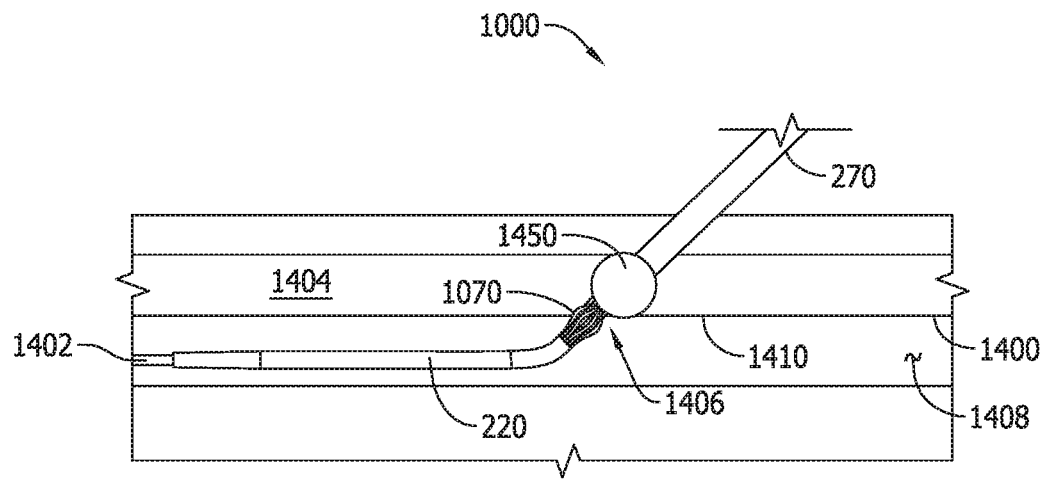
FIG. 17 is a schematic view of a portion of the hemostatic device shown in FIG. 9 dispensing a flowable hemostatic agent, with the exemplary malecot in the stopper configuration shown in FIG. 10 positioned against a wall of the blood vessel.

Further in the exemplary embodiment, flowable hemostatic agent 1450 is dispensed 1350 externally of the vessel lumen, as shown in FIG. 17. For example, flowable hemostatic agent 1450 is injected into injection tube lumen 282 via side port 188 and exits injection tube lumen 282 to the environment via side openings 291. In some embodiments, when exposed outside of hemostatic device 1000, flowable hemostatic agent 1450 forms an elastic coagulome that occludes puncture opening 1406. In at least some implementations, a withdrawal force is maintained on hemostatic device 1000 while flowable hemostatic agent 1450 is dispensed, to ensure that malecot 1070 in the stopper configuration is maintained in abutment against the interior surface of vessel wall 1410.

Figure 18:
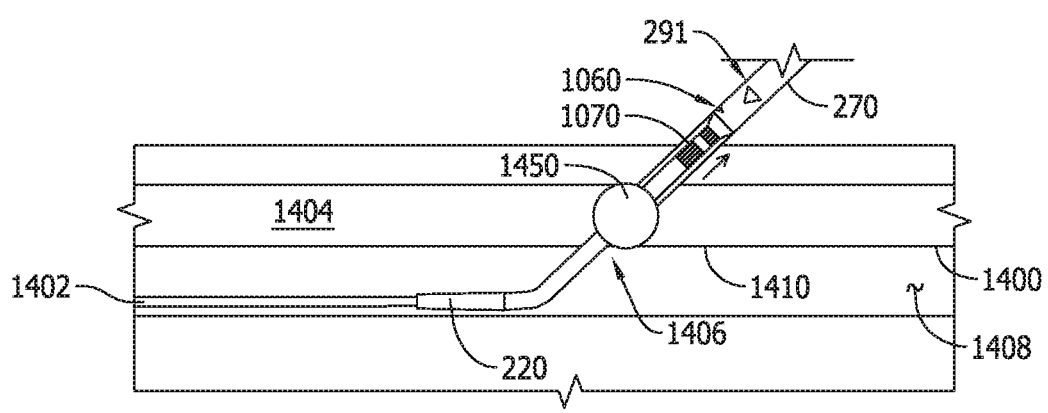
FIG. 18 is a schematic view of a portion of the hemostatic device shown in FIG. 9 being withdrawn from the blood vessel, with the exemplary malecot in the neutral configuration shown in FIG. 9.

In at least some implementations, after flowable hemostatic agent 1450 is dispensed, plug actuator 1090 is selectively moved to second position 1094 such that malecot 1070 is transitioned 1360 to the neutral configuration, as shown in FIG. 18, to facilitate withdrawal 1370 of hemostatic device 1000 from subcutaneous tissue 1404, leaving flowable hemostatic agent 1450 proximate an exterior surface of vessel wall 1410. In the exemplary embodiment, as hemostatic device 1000 is withdrawn, flowable hemostatic agent 1450 is drawn by hemostatic device 1000 along the percutaneous tract away from the surface of vessel wall 1410 and in direction of the skin. Finally, when hemostatic device 1000 is withdrawn, pressure is applied over puncture opening 1406 until hemostasis is achieved.

Figure 19:
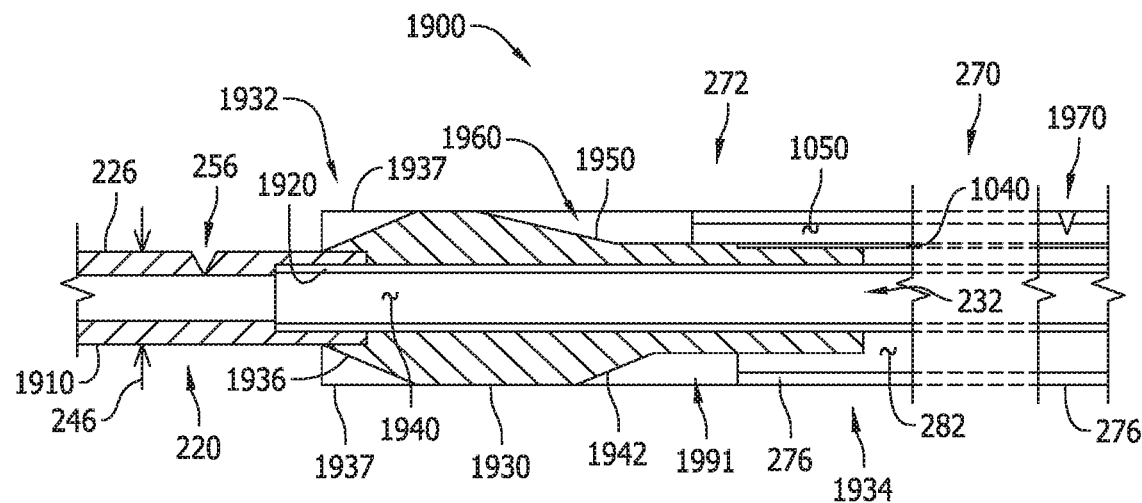
FIG. 19 is a cross-sectional view of a portion of another exemplary hemostatic device.

FIG. 19 is a cross-sectional view of a portion of another exemplary hemostatic device 1900 for sealing a puncture of a vessel (not shown). Hemostatic device 1900 is similar to hemostatic device 100, 200, and 1000, and in the absence of a contrary representation, the same reference numbers identify the same or similar elements. Hemostatic device 1900 includes locator device 220 and injection tube 270. In the exemplary embodiment, second section 238 of locator device 220 includes a distal portion 1910 and a proximal portion 1920. In other embodiments, second section 238 may include any suitable number of portions.

Distal portion 1910 and proximal portion 1920 are coupled coaxially and in fluid communication to define lumen 232. In certain embodiments, hemostatic device 1900 is configured such that distal portion 1910 is substantially the only portion of locator device 220 that crosses a vessel wall and enters a lumen of the vessel. In the exemplary embodiment, locator device distal portion 1910 is flexible, enabling it to bend as it crosses the vessel wall and is advanced into the lumen of the vessel, while locator device proximal portion 1920 is substantially rigid. Proximal portion 1920 resists a bending that would be necessary for it to enter the vessel lumen, thus providing a tactile indication (e.g., resistance) that proximal portion 1920 has encountered a wall of the vessel and inhibiting proximal portion 1920 from passing through the vessel wall. In some embodiments, outer diameter 246 of locator device 220 matches the outer diameter of the procedural sheath used during the procedure and, thus, substantially matches the diameter of the puncture opening. In addition, the muscular layer of the vessel wall tends to recoil around locator device 220 to facilitate occluding the puncture site.

Figure 20:
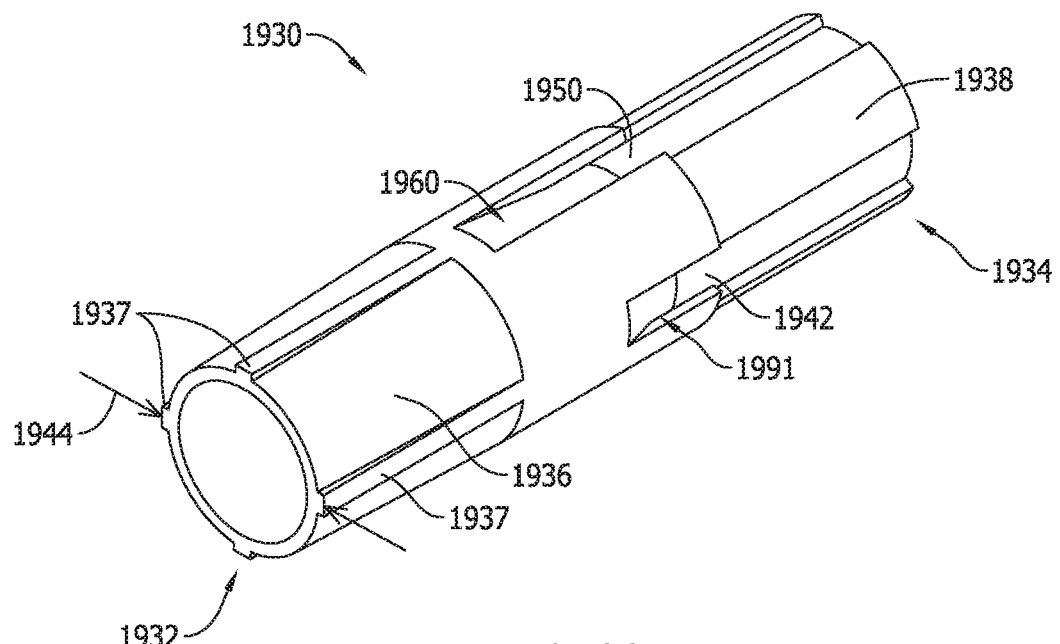
FIG. 20 is a schematic perspective view of an exemplary stopper for use with the exemplary hemostatic device shown in FIG. 19.

In certain embodiments, hemostatic device 1900 includes a substantially rigid stopper 1930 that extends from a proximal end 1934 to a distal end 1932. FIG. 20 is a schematic perspective view of stopper 1930. With reference to FIGS. 19 and 20, stopper 1930 defines a lumen 1940 configured to receive locator device 220 therethrough in an interference fit, such that stopper 1930 is coupled to locator device 220. In the exemplary embodiment, distal end 1932 of stopper 1930 is positioned on locator device 220 proximally of distal opening 256. Moreover, proximal end 1934 of stopper 1930 is coupled to distal end 272 of injection tube 270. For example, in the exemplary embodiment, a proximal portion 1938 of stopper 1930 is sized to be received within an outer diameter of injection tube lumen 282 proximate injection tube distal end 272 in an interference fit.

At least one injection groove 1942 is defined in an outer surface of proximal portion 1938 of stopper 1930. Injection grooves 1942 are each in fluid communication with injection tube lumen 282. Moreover, the at least one injection groove 1942 and injection tube distal end 272 cooperate to define at least one side opening 1991, such that the second fluid is injectable into side port 188, through lumen 282, and dischargeable from side openings 1991 via injection grooves 1942.

In addition, in certain embodiments, a reflux groove 1950 is defined in the outer surface of proximal portion 1938 of stopper 1930. Reflux groove 1950 forms part of a safety reflux system of hemostatic device 1900. More specifically, hemostatic device 1900 includes third or intermediate tube 1040 positioned radially between locator device 220 and side wall 276 of injection tube 270, similar to as described above for hemostatic device 1000. Intermediate tube 1040 is positioned such that third or intermediate lumen 1050 configured to channel blood or, more broadly, a fluid therethrough is at least partially defined by intermediate tube 1040. Moreover, intermediate lumen 1050 is in fluid communication with a second, proximal opening 1970 in injection tube 270. In the exemplary embodiment, second opening 1970 is defined in injection tube 270 similar to as described above for second opening 1170 of hemostatic device 1000 (shown in FIG. 11). For example, but not by way of limitation, second opening 1970 is defined in, and extends through, sidewall 276 of injection tube 270.

Intermediate lumen 1050 is in fluid communication with reflux groove 1950. Moreover, reflux groove 1950 and injection tube distal end 272 cooperate to define a first, stopper reflux opening 1960 in fluid communication with intermediate lumen 1050. Thus, in operation of hemostatic device 1900, fluid may enter through stopper reflux opening 1960, flow via reflux groove 1950 to intermediate lumen 1050, and is dischargeable through second opening 1970. In alternative embodiments, stopper reflux opening 1960, intermediate lumen 1050, and second opening 1970 are defined in any suitable fashion, and at any suitable location, that enables the safety reflux system of hemostatic device 1900 to function as described herein. In other alternative embodiments, hemostatic device 1900 does not include the safety reflux system.

In the exemplary embodiment, reflux groove 1960 and injection grooves 1942 taken together are spaced substantially evenly about a circumference of stopper 1930. For example, in one embodiment, grooves 1942 and 1960 are circumferentially spaced such that side openings 1991 are positioned at each of three quadrants of stopper 1930, and stopper reflux opening 1960 is positioned at a fourth quadrant and aligned with intermediate tube 1040. In alternative embodiments, injection grooves 1942 and reflux groove 1950 are disposed in any suitable fashion that enables hemostatic device 1900 to function as described herein.

In the exemplary embodiment, side openings 1991 are positioned proximal to locator device distal opening 256, such that when distal opening 256 is positioned within a vessel, as evidenced by reflux of a first fluid from locator device proximal side opening 258, side openings 1991 are substantially adjacent, and outside, the vessel to facilitate sealing the puncture of the vessel. Moreover, stopper reflux opening 1960 is positioned proximal to locator device distal opening 256, and side openings 1991 are positioned proximal to stopper reflux opening 1960. Thus, in the exemplary embodiment, an absence of a reflux of the first fluid, for example, blood, from second opening 1970 via intermediate lumen 1050 provides further visual confirmation that stopper reflux opening 1960, and thus side openings 1991 positioned just proximal of stopper reflux opening 1960, are not positioned within a vessel lumen. Stated another way, a reflux of blood through stopper reflux opening 1960, intermediate lumen 1050, and second opening 1970 provides a visual indication that hemostatic device 1900 has been advanced too far into the vessel lumen to permit safe release of the second fluid from side openings 1991.

In the exemplary embodiment, a distal portion 1936 of stopper 1930 is tapered distally to define a smooth transition between distal end 272 of injection tube 270 and locator device 220, facilitating traversal of stopper 1930 through subcutaneous tissue. Additionally in the exemplary embodiment, an outer surface of distal portion 1936 includes a plurality of longitudinally extending ridges 1937 spaced circumferentially about distal portion 1936. Ridges 1937 are configured to provide a tactile indication (e.g., resistance) that stopper 1930 has encountered a wall of the vessel, and to inhibit stopper 1930 from passing through the vessel wall, to further facilitate safe release of the second fluid from side openings 1991. For example, in the exemplary embodiment, ridges 1937 define an outer diameter 1944 that is larger than outer diameter 246 of locator device 220 and, thus, larger than a diameter of the vessel puncture opening. In alternative embodiments, distal portion 1936 has any suitable shape that enables hemostatic device 1900 to function as described herein.

In some embodiments, distal portion 1936 of stopper 1930 includes a radio opaque material, such that distal portion 1936 is identifiable under fluoroscopy to enable further verification that stopper side openings 1991 are positioned outside the vessel lumen. In alternative embodiments, distal portion 1936 does not include a radio opaque material.

Figure 21:
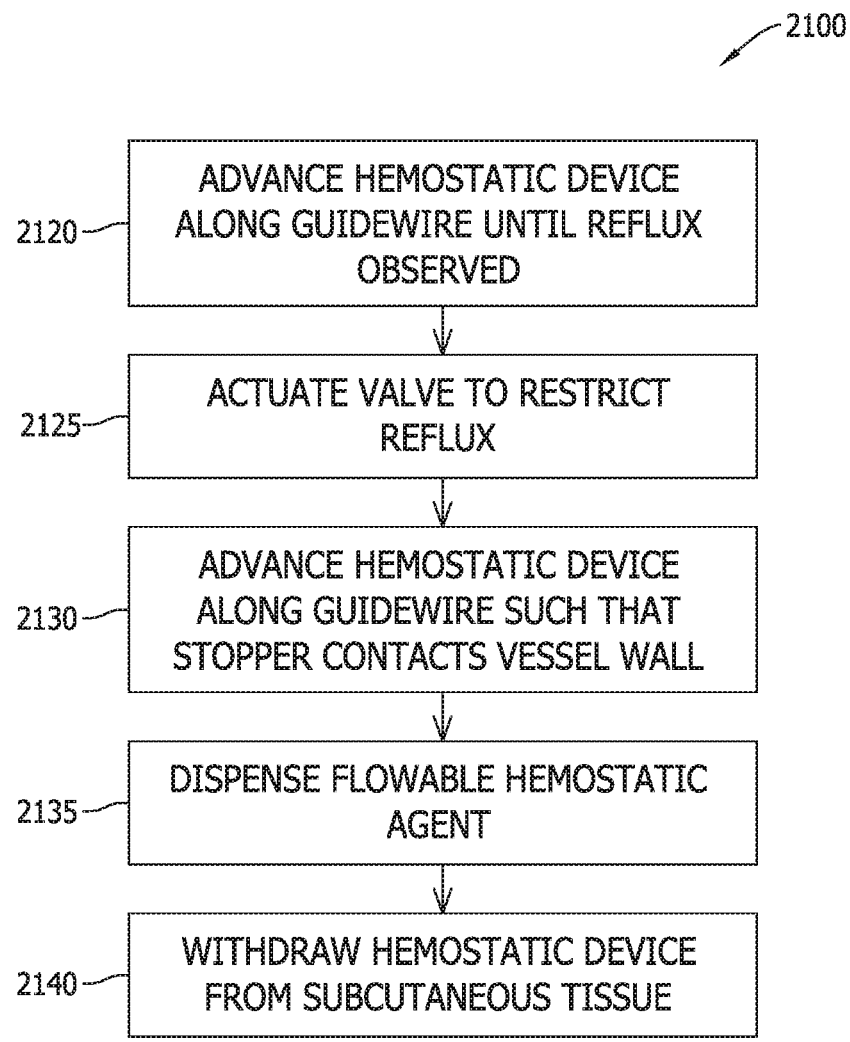
FIG. 21 is a flow chart illustrating an exemplary method of using the exemplary hemostatic device shown in FIG. 19.

FIG. 21 is a flow chart illustrating an exemplary method 2100 of using hemostatic device 1900 to seal puncture opening 1406 in artery or vessel 1400 with flowable hemostatic agent 1450. FIGS. 22-25 illustrate hemostatic device 1900 during various stages of method 2100.

Figure 22:
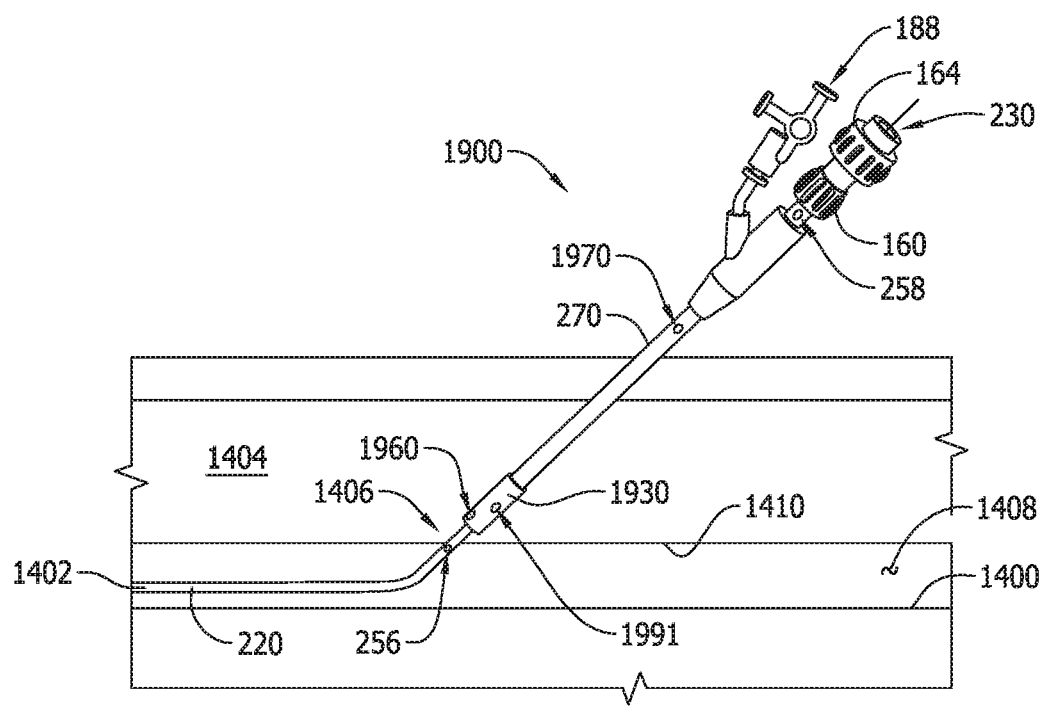
FIG. 22 is a schematic view of the hemostatic device shown in FIG. 19 being advanced into a blood vessel.

During operation, locator device 220 is aligned such that guidewire 1402 extends through distal opening 228, lumen 232, and proximal opening 230. Hemostatic device 1900 is advanced 2120 along guidewire 1402, as shown in FIG. 22, through subcutaneous tissue 1404 into lumen 1408 of vessel 1400 until blood is channeled through locator device first opening 256 and locator device lumen 232 and discharged from at least one of locator device second opening 258 and locator device proximal opening 230. In the exemplary embodiment, the blood discharge (i.e., reflux) is a visual indication that locator device first opening 256 is positioned within vessel 1400, and thus that stopper side openings 1991 are positioned outside and adjacent vessel wall 1410, as shown in FIG. 22. To reduce an amount of blood that refluxes through second opening 258 and/or proximal opening 230, first device valve 160 and/or second device valve 164, respectively, is actuated 2125 to the closed position to restrict the blood from flowing through lumen 232 and out from second opening 258 and/or proximal opening 230.

Figure 23:
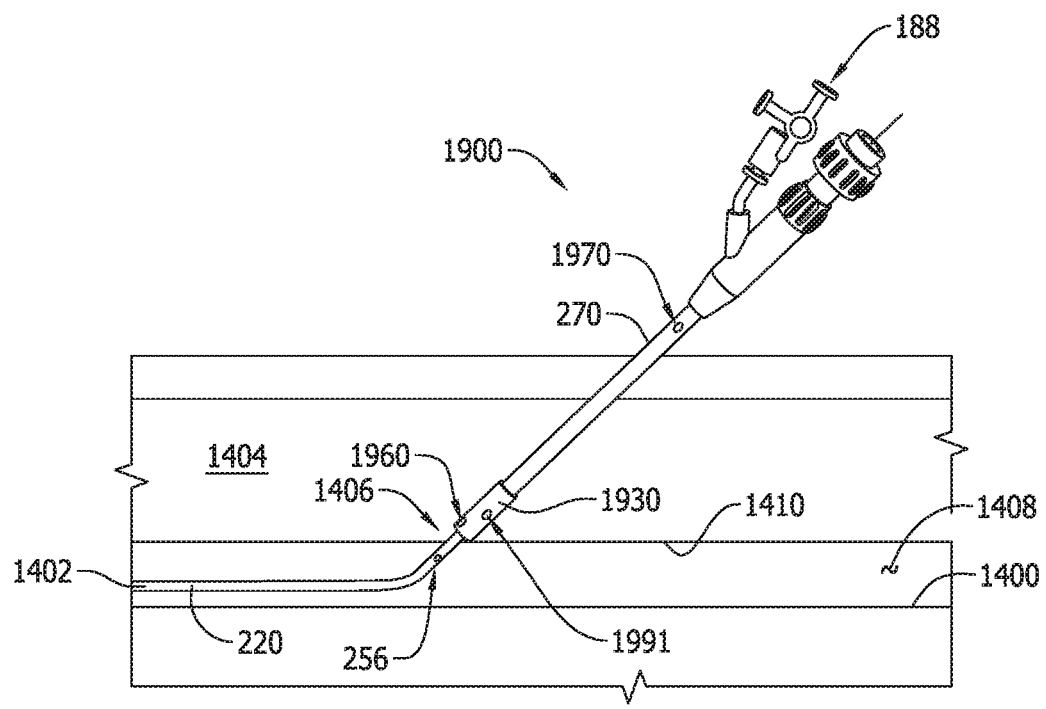
FIG. 23 is a schematic view of the hemostatic device shown in FIG. 19 positioned within the blood vessel, and with the exemplary stopper shown in FIG. 20 positioned against a wall of the blood vessel.

In at least some implementations, hemostatic device 1900 is further advanced 2130 along guidewire 1402 such that stopper 1930 contacts vessel wall 1410, as shown in FIG. 23, providing a tactile indication (i.e., resistance) that stopper side openings 1991 are positioned outside and adjacent vessel wall 1410. In certain implementations, such resistance is enhanced due to longitudinal ridges 1937 contacting vessel wall 1410. Additionally or alternatively, such resistance is enhanced due to rigid locator device proximal portion 1920 crossing vessel wall 1410. Stopper 1930 in contact with vessel wall 1410 further occludes puncture opening 1406 and facilitates ensuring that flowable hemostatic agent 1450 will be released outside vessel lumen 1408.

Moreover, in some implementations, no blood is seen refluxing out of proximal side hole 1970 of injection tube 270 from stopper reflux opening 1960, further verifying that stopper side openings 1991 are positioned outside and adjacent vessel wall 1410. In alternative implementations, blood is seen refluxing out of proximal side hole 1970 via injection tube intermediate lumen 1050 and stopper reflux opening 1960, indicating that stopper 1930 is positioned too far within vessel lumen 1408 and that hemostatic device 1900 should be at least partially withdrawn prior to injection of flowable hemostatic agent 1450 through side port 188. In other alternative embodiments, hemostatic device 1900 does not include stopper reflux opening 1960, injection tube intermediate lumen 1050, and injection tube proximal side hole 1970.

Additionally or alternatively, a contrast fluid is injected through side port 188, injection tube lumen 282, and out of stopper side openings 1991 and viewed 2140 under fluoroscopy to verify that stopper side openings 1991 are positioned outside and adjacent vessel wall 1410. Additionally or alternatively, a radio opaque material of distal portion 1936 of stopper 1930 is viewed 2150 under fluoroscopy to verify that stopper side openings 1991 are positioned outside and adjacent vessel wall 1410.

Figure 24:
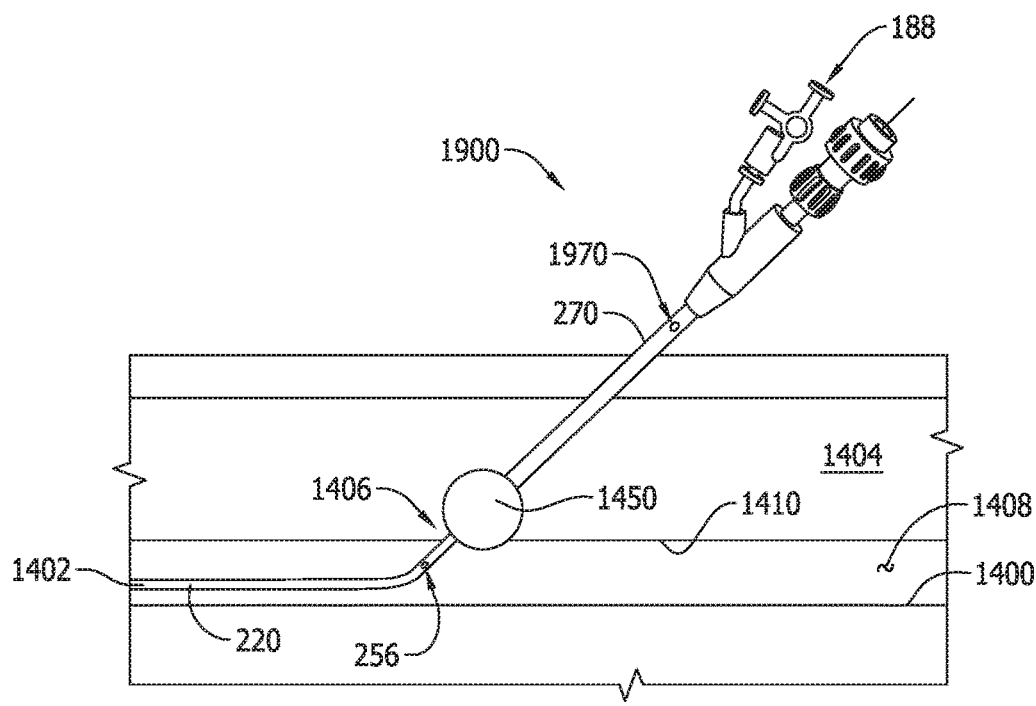
FIG. 24 is a schematic view of the hemostatic device shown in FIG. 19 dispensing a flowable hemostatic agent adjacent the wall of the blood vessel.

Further in the exemplary embodiment, flowable hemostatic agent 1450 is dispensed 2135 externally of vessel lumen 1408, as shown in FIG. 24. For example, flowable hemostatic agent 1450 is injected into injection tube lumen 282 via side port 188, flows into stopper grooves 1942, and exits to the environment via stopper side openings 1991. In some embodiments, when exposed outside of hemostatic device 1900, flowable hemostatic agent 1450 forms an elastic coagulome that occludes puncture opening 1406.

Figure 25:
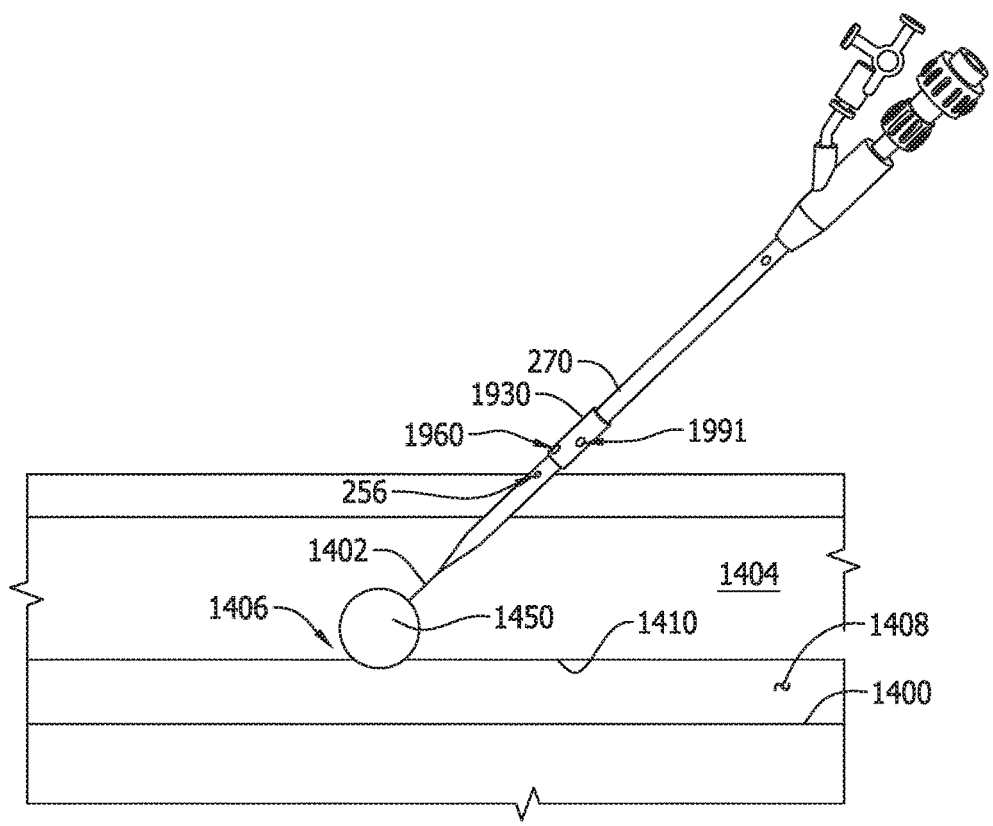
FIG. 25 is a schematic view of the hemostatic device shown in FIG. 19 being withdrawn from the blood vessel.

In at least some implementations, after flowable hemostatic agent 1450 is dispensed, hemostatic device 1900 is withdrawn 2140 from subcutaneous tissue 1404, leaving flowable hemostatic agent 1450 proximate an exterior surface of vessel wall 1410, as shown in FIG. 25. In the exemplary embodiment, as hemostatic device 1900 is withdrawn, flowable hemostatic agent 1450 is drawn by hemostatic device 1900 along the percutaneous tract away from the surface of vessel wall 1410 and in direction of the skin. Finally, when hemostatic device 1900 is withdrawn, pressure is applied over puncture opening 1406 until hemostasis is achieved.

The methods and apparatus described herein relate to medical devices and, more particularly, to a hemostatic device. The methods and apparatus described herein facilitate sealing, for example, an arterial opening. Embodiments of the methods and apparatus described herein include a hemostatic device that includes a first tube defining a first lumen, a second tube circumscribing at least a portion of the first tube and at least partially defining a second lumen configured to dispense a flowable hemostatic agent external to the arterial opening, and at least one reflux system to facilitate proper positioning of the device prior to dispensing the flowable hemostatic agent. At least some embodiments include a malecot that is selectively actuatable between a neutral configuration and a stopper configuration. The malecot is transitioned to the stopper configuration to facilitate occluding the arterial opening, prior to the second tube dispensing at least some of the flowable hemostatic agent to the environment. Additionally, at least some embodiments include a rigid stopper to facilitate occluding the arterial opening. in some embodiments, the rigid stopper includes ridges to provide a tactile indication that the hemostatic device is properly positioned before the second tube dispenses at least some of the flowable hemostatic agent to the environment. In certain embodiments, the rigid stopper includes a safety reflux opening in fluid communication with a third lumen defined by the second tube to facilitate confirmation of proper positioning of the device prior to dispensing the flowable hemostatic agent. The hemocoagulant agent facilitates sealing the arterial opening to reduce a time required for hemostasis and/or ambulation.

The methods and systems described herein relate to medical devices and, more particularly, to a hemostatic device. The hemostatic device described herein facilitates sealing a puncture of a vessel. More particularly, the hemostatic device enables positioning an injection tube adjacent the vessel to inject a gelatin through the injection tube. As such, the hemostatic device facilitates reducing a time required for hemostasis and ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

As used herein, an element or step recited in the singular and proceeded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for sealing a puncture of a vessel using a hemostatic device that includes a first tube defining a first lumen, a malecot coupled to the first tube, a second tube circumscribing at least a portion of the first tube and at least partially defining a second lumen, a third tube at least partially defining a third lumen, and a transfer member coupled to the malecot, wherein the first lumen is configured to receive a guidewire, said method comprising:
   advancing a distal end of the hemostatic device into the vessel until a fluid is channeled through a first opening into the third lumen, wherein the first opening is defined in a side wall of the second tube and positioned proximally relative the malecot;
   transitioning the malecot from a neutral configuration to a stopper configuration by longitudinally positioning the transfer member with respect to the first tube, wherein the transfer member comprises a tube disposed coaxially with, and radially outwardly from, the first tube;
   withdrawing the hemostatic device until the malecot abuts an interior surface of a vessel wall; and
   dispensing a flowable hemostatic agent through the second lumen and out of a second opening defined in the side wall of the second tube.

2. A method in accordance with claim 1, wherein transitioning the malecot from the neutral configuration to the stopper configuration further comprises increasing a diameter of the malecot from a first diameter to a second diameter, the second diameter is greater than a diameter of the puncture.

3. A method in accordance with claim 1, wherein transitioning the malecot from the neutral configuration to the stopper configuration further comprises selectively operating a plug actuator coupled to the hemostatic device.

4. A method in accordance with claim 1, wherein the malecot comprises a plurality of deformable segments, and wherein longitudinally positioning the transfer member with respect to the first tube further comprises reversibly deforming the plurality of deformable segments radially outward from the first tube.

5. A method in accordance with claim 1, further comprising:
   transitioning the malecot from the stopper configuration to the neutral configuration; and
   withdrawing the hemostatic device from the vessel.

6. A method in accordance with claim 1, wherein the second tube includes a proximal opening in fluid communication with the second opening, and wherein dispensing the flowable hemostatic agent through the second lumen further comprises injecting the second fluid into the second lumen via the proximal opening.

7. A hemostatic device for sealing a puncture of a vessel, said hemostatic device comprising:
   a first tube defining a first lumen, the first lumen configured to receive a guidewire;
   a malecot coupled to the first tube, the malecot selectively actuatable from a neutral configuration to a stopper configuration;
   a transfer member coupled to the malecot, the transfer member longitudinally positionable with respect to the first tube to transition the malecot from the neutral configuration to the stopper configuration, wherein the transfer member comprises a tube disposed coaxially with, and radially outwardly from, the first tube;
   a second tube circumscribing at least a portion of the first tube and at least partially defining a second lumen; and a third tube at least partially defining a third lumen, wherein the second tube comprises a first opening and a second opening each defined in a side wall of the second tube, the first opening in flow communication with the third lumen and the second opening in flow communication with the second lumen, wherein the first opening is positioned proximally relative to the malecot, and wherein the second lumen is configured to dispense a flowable hemostatic agent from the second opening.

8. A hemostatic device in accordance with claim 7, further comprising:
   a housing; and
   a plug actuator coupled to the housing, the plug actuator operable to selectively transition the malecot between the neutral configuration and the stopper configuration.

9. A hemostatic device in accordance with claim 7, wherein the transfer member is selectively operable for longitudinal translation with respect to the first tube by a plug actuator coupled to a housing of the hemostatic device.

10. A hemostatic device in accordance with claim 7, wherein the malecot comprises a plurality of deformable segments, the transfer member configured to reversibly deform the plurality of deformable segments radially outward from the first tube to transition the malecot from the neutral configuration to the stopper configuration.

11. A hemostatic device in accordance with claim 10, wherein the malecot further comprises a distal portion rigidly coupled to the first tube, the plurality of deformable segments is disposed between the malecot distal portion and the transfer member.

12. A hemostatic device in accordance with claim 11, wherein the transfer member, the malecot distal portion, and the plurality of deformable segments are formed unitarily from a single tube.

13. A hemostatic device in accordance with claim 7, wherein the second tube further comprises a proximal opening configured to receive the flowable hemostatic agent, the proximal opening in flow communication with the second opening.

14. A hemostatic device for sealing a puncture of a vessel, said hemostatic device comprising:
   a first tube defining a first lumen, the first lumen configured to receive a guidewire;
   a malecot coupled to the first tube;
   a second tube circumscribing at least a portion of the first tube and at least partially defining a second lumen;
   a third tube at least partially defining a third lumen, wherein the second tube comprises a first opening and a second opening each defined in a side wall of the second tube, the first opening in flow communication with the third lumen and the second opening in flow communication with the second lumen, wherein the first opening is positioned proximally relative to the malecot, and wherein the second lumen is configured to dispense a flowable hemostatic agent from the second opening;
   a plug actuator configured to transition the malecot from a neutral configuration to a stopper configuration; and
   a transfer member selectively operable by the plug actuator for longitudinal translation with respect to the first tube to transition the malecot from the neutral configuration to the stopper configuration, wherein the transfer member comprises a tube disposed coaxially with, and radially outwardly from, the first tube.

15. A hemostatic device in accordance with claim 14, wherein the malecot comprises a plurality of deformable segments, the transfer member configured to reversibly deform the plurality of deformable segments radially outward from the first tube to transition the malecot from the neutral configuration to the stopper configuration.

* * * * *